United States Patent
Becker et al.

(10) Patent No.: US 7,641,779 B2
(45) Date of Patent: *Jan. 5, 2010

(54) METHOD AND APPARATUS FOR PROGRAMMABLE FLUIDIC PROCESSING

(75) Inventors: Frederick F. Becker, Houston, TX (US); Peter Gascoyne, Bellaire, TX (US); Xiaobo Wang, Sugarland, TX (US); Jody Valentine Vykoukal, Houston, TX (US); Giovanni De Gasperis, L'Aquila (IT)

(73) Assignee: Board of Regents, The University of Texas System, Austin, TX (US)

( * ) Notice: Subject to any disclaimer, the term of this patent is extended or adjusted under 35 U.S.C. 154(b) by 534 days.

This patent is subject to a terminal disclaimer.

(21) Appl. No.: 11/135,615

(22) Filed: May 23, 2005

(65) Prior Publication Data

US 2006/0070879 A1  Apr. 6, 2006

Related U.S. Application Data

(63) Continuation of application No. 09/902,933, filed on Jul. 10, 2001, now Pat. No. 6,977,033, which is a continuation of application No. 09/249,955, filed on Feb. 12, 1999, now Pat. No. 6,294,063.

(51) Int. Cl.
*G01N 27/447* (2006.01)
*G01N 27/453* (2006.01)

(52) U.S. Cl. .................... 204/547; 204/643

(58) Field of Classification Search ............... 204/450, 204/600, 547, 643
See application file for complete search history.

(56) References Cited

U.S. PATENT DOCUMENTS

| 4,390,403 A | 6/1983 | Batchelder | 204/547 |
| 4,418,346 A | 11/1983 | Batchelder | 345/107 |
| 4,619,670 A | 10/1986 | Malcolm et al. | 96/27 |
| 4,661,451 A * | 4/1987 | Hansen | 435/174 |
| 4,789,803 A | 12/1988 | Jacobsen et al. | 310/309 |
| 4,887,721 A | 12/1989 | Martin et al. | 205/579 |
| 4,896,174 A | 1/1990 | Stearns | 347/120 |

(Continued)

FOREIGN PATENT DOCUMENTS

DE  3931851 A  4/1991

(Continued)

OTHER PUBLICATIONS

Fluri et al., "Integrated capillary electrophoresis devices with an efficient postcolumn reactor in planar quartz and glass chips," *Anal. Chem.*, 68:4285-4290, Dec. 1996.

(Continued)

*Primary Examiner*—Alex Noguerola
(74) *Attorney, Agent, or Firm*—Fulbright & Jaworski

(57) ABSTRACT

A method and apparatus for microfluidic processing by programmably manipulating a packet. A material is introduced onto a reaction surface and compartmentalized to form a packet. A position of the packet is sensed with a position sensor. A programmable manipulation force is applied to the packet at the position. The programmable manipulation force is adjustable according to packet position by a controller. The packet is programmably moved according to the programmable manipulation force along arbitrarily chosen paths.

16 Claims, 11 Drawing Sheets

U.S. PATENT DOCUMENTS

| | | | |
|---|---|---|---|
| 4,908,112 A | 3/1990 | Pace | 210/198.2 |
| 5,100,627 A | 3/1992 | Buican et al. | 422/108 |
| 5,126,022 A | 6/1992 | Soane et al. | 204/458 |
| 5,180,480 A | 1/1993 | Manz | 204/644 |
| 5,250,263 A | 10/1993 | Manz | 422/81 |
| 5,284,471 A | 2/1994 | Sage | 604/20 |
| 5,296,114 A | 3/1994 | Manz | 204/180 |
| 5,344,535 A | 9/1994 | Betts et al. | 204/183.1 |
| 5,364,744 A | 11/1994 | Buican et al. | 430/321 |
| 5,427,663 A | 6/1995 | Austin et al. | 204/180.1 |
| 5,454,472 A | 10/1995 | Benecke et al. | 209/127.1 |
| 5,489,506 A | 2/1996 | Crane | 435/2 |
| 5,532,129 A | 7/1996 | Heller | 435/6 |
| 5,565,322 A | 10/1996 | Heller | 435/6 |
| 5,569,367 A | 10/1996 | Betts et al. | 204/547 |
| 5,569,591 A | 10/1996 | Kell et al. | 435/29 |
| 5,580,435 A | 12/1996 | Kovacs | 204/603 |
| 5,582,701 A | 12/1996 | Geis et al. | 204/451 |
| 5,585,069 A | 12/1996 | Zanzucchi et al. | 422/100 |
| 5,603,351 A | 2/1997 | Cherukuri et al. | 137/597 |
| 5,605,662 A | 2/1997 | Heller et al. | 422/68.1 |
| 5,632,957 A | 5/1997 | Heller et al. | 422/68.1 |
| 5,653,859 A | 8/1997 | Parton et al. | 204/450 |
| 5,681,484 A | 10/1997 | Zanzucchi et al. | 216/2 |
| 5,683,569 A | 11/1997 | Chung et al. | 205/775 |
| 5,750,015 A | 5/1998 | Soane et al. | 204/454 |
| 5,795,457 A | 8/1998 | Pethig et al. | 204/547 |
| 5,814,200 A | 9/1998 | Pethig et al. | 204/547 |
| 5,849,486 A | 12/1998 | Heller et al. | 435/6 |
| 5,858,195 A | 1/1999 | Ramsey | 204/601 |
| 5,948,328 A * | 9/1999 | Fiedler et al. | 264/5 |
| 5,993,631 A | 11/1999 | Parton et al. | 204/547 |
| 6,017,696 A | 1/2000 | Heller | 435/6 |
| 6,027,623 A | 2/2000 | Ohkawa | 204/450 |
| 6,051,380 A | 4/2000 | Sosnowski et al. | 435/6 |
| 6,068,818 A | 5/2000 | Ackley et al. | 422/50 |
| 6,071,394 A | 6/2000 | Cheng et al. | 204/547 |
| 6,084,503 A | 7/2000 | Ruile et al. | 340/10.1 |
| 6,099,803 A | 8/2000 | Ackley et al. | 422/68.1 |
| 6,113,768 A | 9/2000 | Fuhr et al. | 204/643 |
| 6,129,828 A | 10/2000 | Sheldon, III et al. | 204/518 |
| 6,149,789 A | 11/2000 | Benecke et al. | 204/547 |
| 6,156,181 A | 12/2000 | Parce et al. | 204/600 |
| 6,169,394 B1 | 1/2001 | Frazier et al. | 324/71.4 |
| 6,294,063 B1 | 9/2001 | Becker et al. | 204/405 |
| 6,977,033 B2 * | 12/2005 | Becker et al. | 204/450 |

FOREIGN PATENT DOCUMENTS

| | | |
|---|---|---|
| WO | WO 97/20210 | 6/1997 |
| WO | WO 97/34689 | 9/1997 |
| WO | WO 98/04355 | 2/1998 |
| WO | WO 99/62622 | 12/1999 |
| WO | WO 00/69565 | 11/2000 |
| WO | WO 01/05511 | 1/2001 |
| WO | WO 01/05512 | 1/2001 |
| WO | WO 01/05513 | 1/2001 |
| WO | WO 01/05514 | 1/2001 |

OTHER PUBLICATIONS

Latta, "Miniaturization, parallel processing come to lab devices," *The Scientist*, Internet: www.the-scientist.library.upenn.edu, Sep. 1997.

Li and Harrison, "Transport, manipulation, and reaction of biological cells on-chip using electrokinetic effects," *Anal. Chem.*, 69:1564-1568, Apr. 1997.

"Platform technology may have broad applicability for facilitating preparation and analysis of DNA/RNA from mixed cell test samples," *Nature Biotech.*, Internet: www.nanogen.com, 1998.

Schmalzing et al., "DNA typing in thirty seconds with a microfabricated device," *Proc. Natl. Acad. Sci. USA*, 94:10273-10278, Sep. 1997.

"Technology," *Nanogen*, Internet: www.nanogen.com, Nov. 1998.

Fiedler et al., "Dielectrophoretic sorting of particles and cells in a microsystem," *Anal. Chem*, 70:1909-1915, 1998.

Fuhr et al., "Positioning and manipulation of cells and microparticles using miniaturized electric field traps and travelling waves," *Sensors and Materials*, 7:131-146, 1995.

Milner et al., "Dielectrophoretic classification of bacteria using differential impedance measurements," *Electronics Letters*, 34:66-68, 1998.

Nishioka et al., "Micro manipulation of cells and DNA molecules," *J. Electrostatics*, 35:83-91, 1995.

Washizu, "Electrostatic actuation of liquid droplets for microreactor applications," *IEEE Transactions on Ind. Appl.*, 34:732-737, 1998.

Cheng et al., "Preparation and hybridizaton analysis of DNA/RNA from *E. coli* on microfrabricated bioelectronic chips," *Nature Biotech.*, 16:541-546, Jun. 1998.

Moesner and Higuchi, "Electrostatic devices for particle micro-handling," *Industry Applications Conference*, 13th IAS Annual Meeting, Orlando, FL, Oct. 8-12, 1995.

* cited by examiner

METHOD AND APPARATUS FOR PROGRAMMABLE FLUIDIC PROCESSING

This application is a continuation of U.S. application Ser. No. 09/902,933 filed Jul. 10, 2001 now U.S. Pat. No. 6,977,033, which is a continuation of U.S. application Ser. No. 09/249,955, filed Feb. 12, 1999 (and now issued as U.S. Pat. No. 6,294,063).

BACKGROUND OF THE INVENTION

1. Field of the Invention

The present invention relates generally to fluidic processing and, more particularly, to a method and apparatus for programmably manipulating and interacting one or more compartmentalized packets of material on a reaction surface.

2. Description of Related Art

Chemical protocols often involve a number of processing steps including metering, mixing, transporting, division, and other manipulation of fluids. For example, fluids are often prepared in test tubes, metered out using pipettes, transported into different test tubes, and mixed with other fluids to promote one or more reactions. During such procedures, reagents, intermediates, and/or final reaction products may be monitored, measured, or sensed in analytical apparatus. Microfluidic processing generally involves such processing and monitoring using minute quantities of fluid. Microfluidic processing finds applications in vast fields of study and industry including, for instance, diagnostic medicine, environmental testing, agriculture, chemical and biological warfare detection, space medicine, molecular biology, chemistry, biochemistry, food science, clinical studies, and pharmaceutical pursuits.

A current approach to fluidic and microfluidic processing utilizes a number of microfluidic channels that are configured with microvalves, pumps, connectors, mixers, and detectors. While devices using micro-scale implementations of these traditional approaches may exhibit at least a degree of utility, vast room for improvement remains. For instance, pumps and valves used in traditional fluidic transportation are mechanical. Mechanical devices, particularly when coupled to thin microchannels, may be prone to failure or blockage. In particular, thin channels may become narrowed or partially-blocked due to buildup of channel contamination, which, in turn, may lead to mechanical failure of associated devices. Current microfluidic devices also lack flexibility, for they rely upon a fixed pathway of microchannels. With fixed pathways, devices are limited in the number and type of tasks they may perform. Also, using fixed pathways makes many types of metering, transport, and manipulation difficult. With traditional devices, it is difficult to partition one type of sample from another within a channel.

Electrical properties of materials have been employed to perform a limited number of fluidic processing tasks. For example, dielectrophoresis has been utilized to aid in the characterization and separation of particles, including biological cells. An example of such a device is described in U.S. Pat. No. 5,344,535 to Betts, incorporated herein by reference. Betts establishes dielectrophoretic collection rates and collection rate spectra for dielectrically polarizable particles in a suspension. Particle concentrations at a certain location downstream of an electrode structure are measured using a light source and a light detector, which measures the increased or decreased absorption or scattering of the light which, in turn, indicates an increase or decrease in the concentration of particles suspended in the fluid. Although useful for determining particle dielectrophoretic properties, such a system is limited in application. In particular, such a system does not allow for general fluidic processing involving various interactions, sometimes performed simultaneously, such as metering, mixing, fusing, transporting, division, and general manipulation of multiple reagents and reaction products.

Another example of using certain electrical properties for specific types of processing is disclosed in U.S. Pat. No. 5,632,957 to Heller et al., incorporated herein by reference. There, controlled hybridization may be achieved using a matrix or array of electronically addressable microlocations in conjunction with a permeation layer, an attachment region and a reservoir. An activated microlocation attracts charged binding entities towards an electrode. When the binding entity contacts the attachment layer, which is situated upon the permeation layer, the functionalized specific binding entity becomes covalently attached to the attachment layer. Although useful for specific tasks such as DNA hybridization, room for improvement remains. In particular, such a system, utilizing attachment sites for certain binding entities is designed for particular applications and not for general fluidic processing of a variety of fluids. More specifically, such a system is designed for use with charged binding entities that interact with attachment sites.

Another example of processing is disclosed in U.S. Pat. No. 5,126,022 to Soane et al., incorporated herein by reference. There, charged molecules may be moved through a medium that fills a trench in response to electric fields generated by electrodes. Although useful for tasks such as separation, room for improvement remains in that such devices are not well suited for performing a wide variety of fluidic processing interactions on a wide variety of different materials.

There are other examples of using dielectrophoresis for performing specific, limited fluidic processing tasks. U.S. Pat. No. 5,795,457 to Pethig and Burt, incorporated herein by reference, disclose a method for promoting reactions between particles suspended in liquid by applying two or more electrical fields of different frequencies to electrode arrays. While perhaps useful for facilitating certain interactions between many particles of different types, the method is not well suited for general fluidic processing. U.S. Pat. No. 4,390,403 to Batchelder, incorporated herein by reference, discloses a method and apparatus for manipulation of chemical species by dielectrophoretic forces. Although useful for inducing certain chemical reactions, its flexibility is limited, and it does not allow for general, programmable fluidic processing.

Any problems or shortcomings enumerated in the foregoing are not intended to be exhaustive but rather are among many that tend to impair the effectiveness of previously known processing techniques. Other noteworthy problems may also exist; however, those presented above should be sufficient to demonstrated that apparatus and methods appearing in the art have not been altogether satisfactory.

SUMMARY OF THE INVENTION

In one respect, the invention is an apparatus for programmably manipulating a packet. As used herein, "packet" refers to compartmentalized matter and may refer to a fluid packet, an encapsulated packet, and/or a solid packet. A fluid packet refers to one or more packets of liquids or gases. A fluid packet may refer to a droplet or bubble of a liquid or gas. A fluid packet may refer to a droplet of water, a droplet of reagent, a droplet of solvent, a droplet of solution, a droplet of sample, a particle or cell suspension, a droplet of an intermediate product, a droplet of a final reaction product, or a droplet of any material. An example of a fluid packet is a droplet of aqueous solution suspended in oil. An encapsulated packet refers to a packet enclosed by a layer of material. An encapsulated packet may refer to vesicle or other microcapsule of liquid or gas that may contain a reagent, a sample, a particle, a cell, an intermediate product, a final reaction product, or any material. The surface of an encapsulated packet may be coated with a reagent, a sample, a particle or cell, an intermediate product, a final reaction product, or any material. An example of an encapsulated packet is a lipid vesicle containing an aqueous solution of reagent suspended in water. A solid packet refers to a solid material that may contain, or be covered with a reagent, a sample, a particle or cell, an intermediate product, a final reaction product, or any material. An example of a solid packet is a latex microsphere with reagent bound to its surface suspended in an aqueous solution. Methods for producing packets as defined herein are known in the art. Packets may be made to vary greatly in size and shape, but in embodiments described herein, packets may have a diameter between about 100 nm and about 1 cm.

In this respect, the invention includes a reaction surface, an inlet port, means for generating a programmable manipulation force upon the packet, a position sensor, and a controller. The reaction surface is configured to provide an interaction site for the packet. The inlet port is coupled to the reaction surface and is configured to introduce the packet onto the reaction surface. The means for generating a programmable manipulation force upon the packet programmably moves the packet about the reaction surface along arbitrarily chosen paths. As used herein, by "arbitrarily chosen paths" it is meant that paths may be chosen to have any shape about the reaction surface. Arbitrarily chosen paths are not limited to movements that are predefined. Arbitrarily chosen paths may be modified in an unlimited manner about the reaction surface and may hence trace out any pattern. The position sensor is coupled to the reaction surface and is configured to sense a position of the packet on the reaction surface. The controller is coupled to the means for generating a programmable manipulation force and to the position sensor. The controller is configured to adjust the programmable manipulation force according to the position.

In other aspects, the apparatus may also include an outlet port coupled to the reaction surface. The outlet port may be configured to collect the packet from the reaction surface. The means for generating a manipulation force may include a conductor adapted to generate an electric field. The means for generating a manipulation force may include a light source. The manipulation force may include a dielectrophoretic force, an electrophoretic force, an optical force, a mechanical force, or any combination thereof. The position sensor may include a conductor configured to measure an electrical impedance of the packet. The position sensor may include an optical system configured to monitor the position of the packet. The means for generating a programmable manipulation force and the position sensor may be integral.

In another respect, the invention is an apparatus for microfluidic processing by programmably manipulating packets. The apparatus includes a reaction surface, an inlet port, an array of driving electrodes, and an array of impedance sensing electrodes. As used herein, an "array" refers to any grouping or arrangement. An array may be a linear arrangement of elements. It may also be a two dimensional grouping having columns and rows. Columns and rows need not be uniformly spaced or orthogonal. An array may also be any three dimensional arrangement. The reaction surface is configured to provide an interaction site for the packets. The inlet port is coupled to the reaction surface and is configured to introduce the packets onto the reaction surface. The array of driving electrodes is coupled to the reaction surface and is configured to generate a programmable manipulation force upon the packets to direct the microfluidic processing by moving the packets along arbitrarily chosen paths. The array of impedance sensing electrodes is coupled to the reaction surface and is configured to sense positions of the packets during the microfluidic processing.

In other aspects, the apparatus may also include an outlet port coupled to the reaction surface. The outlet port may be configured to collect the packets from the reaction surface. The apparatus may also include a controller coupled to the array of driving electrodes and to the array of impedance sensing electrodes. The controller may be adapted to provide a feedback from the array of impedance sensing electrodes to the array of driving electrodes. The array of driving electrodes and the array of impedance sensing electrodes may be integral. The apparatus may also include an integrated circuit coupled to the array of driving electrodes and to the array of impedance sensing electrodes. The apparatus may also include a coating modifying a hydrophobicity of the reaction surface. The apparatus may also include a maintenance port.

In another respect, the invention is an apparatus for processing packets in a partitioning medium. As used herein, a "partitioning medium" refers to matter that may be adapted to suspend and compartmentalize other matter to form packets on a reaction surface. A partitioning medium may act by utilizing differences in hydrophobicity between a fluid and a packet. For instance, hydrocarbon molecules may serve as a partitioning medium for packets of aqueous solution because molecules of an aqueous solution introduced into a suspending hydrocarbon fluid will strongly tend to stay associated with one another. This phenomenon is referred to as a hydrophobic effect, and it allows for compartmentalization and easy transport of packets upon or over a surface. A partitioning medium may also be a dielectric carrier liquid which is immiscible with sample solutions. Other suitable partitioning mediums include, but are not limited to, air, aqueous solutions, organic solvents, oils, and hydrocarbons. The apparatus includes a chamber, a programmable dielectrophoretic array, and an impedance sensing array. As used herein, a "programmable dielectrophoretic array" (PDA) refers to an electrode array whose individual elements can be addressed with different electrical signals. The addressing of electrode elements with electrical signals may initiate different field distributions and generate dielectrophoretic manipulation forces that trap, repel, transport, or perform other manipulations upon packets on and above the electrode plane. By programmably addressing electrode elements within the array with electrical signals, electric field distributions and manipulation forces acting upon packets may be programmable so that packets may be manipulated along arbitrarily chosen or predetermined paths. The chamber is configured to contain the packets and the partitioning medium. The programmable dielectrophoretic array is coupled to the chamber and is configured to generate a programmable dielectrophoretic force to direct processing of the packets. The impedance sensing array of electrodes is integral with the programmable dielectrophoretic array. The impedance sensing array of electrodes is configured to sense a position of the packets within the chamber.

In other aspects, the apparatus may also include an integrated circuit coupled to the programmable dielectrophoretic array and to the impedance sensing array of electrodes. The apparatus may also include a controller coupled to the programmable dielectrophoretic array and to the impedance sensing array of electrodes. The controller may be adapted to provide a feedback from the impedance sensing array of electrodes to the programmable dielectrophoretic array. The electrodes may be between about 1 micron and about 200 microns and may be spaced between about 1 micron and about 200 microns.

In another respect, the invention is a method for manipulating a packet in which the following are provided: a reaction surface, an inlet port coupled to the reaction surface, means for generating a programmable manipulation force upon the packet, a position sensor coupled to the reaction surface, and a controller coupled to the means for generating a programmable manipulation force and to the position sensor. A material is introduced onto the reaction surface with the inlet port. The material is compartmentalized to form the packet. A position of the packet is sensed with the position sensor. A programmable manipulation force is applied on the packet at the position with the means for generating a programmable manipulation force. The programmable manipulation force is adjustable according to the position by the controller. The packet is programmably moved according to the programmable manipulation force along arbitrarily chosen paths.

In other aspects, the packet may include a fluid packet, an encapsulated packet, or a solid packet. The compartmentalizing may include suspending the material in a partitioning medium. The material may be immiscible in the partitioning medium. The reaction surface may include a coating, and the hydrophobicity of the coating may be greater than a hydrophobicity of the partitioning medium. The application of the programmable manipulation force may include applying a driving signal to one or more driving electrodes arranged in an array to generate the programmable manipulation force. The programmable manipulation force may include a dielectrophoretic force, an electrophoretic force, an optical force, a mechanical force, or any combination thereof. The sensing of a position may include applying a sensing signal to one or more impedance sensing electrodes arranged in an array to detect an impedance associated with the packet.

In another respect, the invention is a method of fluidic processing in which the following are provided: a reaction surface, an inlet port coupled to the reaction surface, an array of driving electrodes coupled to the reaction surface, and an array of impedance sensing electrodes coupled to the reaction surface. One or more materials are introduced onto the reaction surface with the inlet port. The one or more materials are compartmentalized to form a plurality of packets. A sensing signal is applied to one or more of the impedance sensing electrodes to determine a position of one or more of the plurality of packets. A driving signal is applied to one or more of the driving electrodes to generate a programmable manipulation force on one or more of the plurality of packets at the position. One or more of the plurality of packets are interacted according to the programmable manipulation force.

In other aspects, at least one of the plurality of packets may include a fluid packet, an encapsulated packet, or a solid packet. The sensing signal and the driving signal may be a single processing signal. The processing signal may include a first frequency component corresponding to the sensing signal and a second frequency component corresponding to the driving signal. A packet distribution map may be formed according to the positions of the plurality of packets. A position of one or more obstructions on the reaction surface may be determined. The interacting of one or more packets may include moving, fusing, merging, mixing, reacting, metering, dividing, splitting, sensing, collecting, or any combination thereof.

In another respect, the invention is a method for manipulating one or more packets on a reaction surface in which the following are provided: a programmable dielectrophoretic array coupled to the reaction surface and an impedance sensing array of electrodes integral with the programmable dielectrophoretic array. A material is introduced onto the reaction surface. The material is compartmentalized to form the one or more packets. A path is specified upon the reaction surface. A programmable manipulation force is applied with the programmable dielectrophoretic array on the one or more packets to move the one or more packets along the path. A position of the one or more packets is sensed with the impedance sensing array of electrodes. Whether the position corresponds to the path is monitored. The one or more packets are interacted.

In other aspects, at lease one of the one or more packets may include a fluid packet, an encapsulated packet, or a solid packet. The method may also include sensing a position of an obstruction; determining a modified path, the modified path avoiding the obstruction; and applying a programmable manipulation force on the one or more packets to move the one or more packets along the modified path. The specification of a path may include specifying an initial position and a final position. The introduction of the material may include extracting the material with a dielectrophoretic extraction force from an injector onto the reaction surface. The interacting of one or more packets may include moving, fusing, merging, mixing, reacting, metering, dividing, splitting, sensing, collecting, or any combination thereof.

Other features and advantages of the present invention will become apparent with reference to the following description of typical embodiments in connection with the accompanying drawings wherein like reference numerals have been applied to like elements, in which:

DESCRIPTION OF ILLUSTRATIVE EMBODIMENTS

The disclosed method and apparatus provide many advantages. For instance, they permit the fluidic processing of minute quantities of samples and reagents. The apparatus need not use conventional hardware components such as valves, mixers, pump. The apparatus may be readily miniaturized and its processes may be automated or programmed. The apparatus may be used for many different types of microfluidic processing and protocols, and it may be operated in parallel mode whereby multiple fluidic processing tasks and reactions are performed simultaneously within a single chamber. Because it need not rely on narrow tubes or channels, blockages may be minimized or eliminated. Further, if obstructions do exist, those obstructions may be located and avoided with position sensing techniques.

Allowing for flexible microfluidic processing, the disclosed method and apparatus has vast applications including, but not limited to, blood and urine assays, pathogen detection, pollution monitoring, water monitoring, fertilizer analysis, the detection of chemical and biological warfare agents, food pathogen detection, quality control and blending, massively parallel molecular biological protocols, genetic engineering, oncogene detection, and pharmaceutical development and testing.

Figure 1:
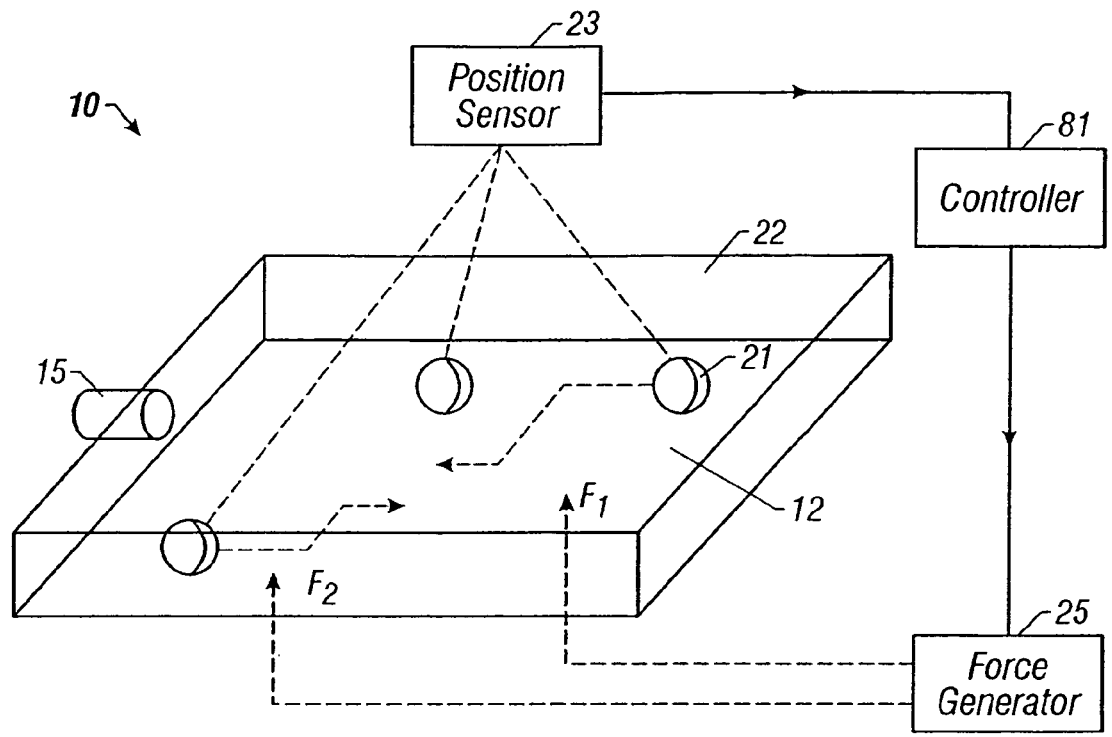
FIG. 1 is a simplified schematic diagram that illustrates a microfluidic device according to one embodiment of the presently disclosed method and apparatus.

In one embodiment of the disclosed method and apparatus, a fluidic device 10 as shown in FIG. 1 is employed. As illustrated, fluidic device 10 may include a reaction surface 12, a port 15, packets 21, wall 22, position sensor 23, a force generator 25, and a controller 81.

In operation, one or more materials may be introduced onto reaction surface 12 through port 15. The one or more materials may be compartmentalized to form packets 21 within a partitioning medium (not shown). Force generator 25 generates a manipulation force on packets 21 to facilitate fluidic manipulations and interactions. In the illustrated embodiment, force generator 25 generates two forces, $F_1$ and $F_2$, that manipulate packets 21 and moves them according to the dashed lines of FIG. 1. Position sensor 23 senses the positions of packets 21 and is able to monitor any packet interactions. As position sensor 23 is coupled to force generator 25 by controller 81, a feedback relationship may be established. Such feedback may include determination of the position of packets 21 on reaction surface 12 that allows for the application of manipulation forces on packets 21 based on position information. The position of packets during manipulation may thus be continuously monitored and this information may be used to continuously adjust one or more manipulation forces so to achieve movement of packets 21 along a desired trajectory to a desired location on reaction surface 12.

In the illustrated embodiment of FIG. 1, forces $F_1$ or $F_2$ may include many different types of forces. For instance, forces $F_1$ and $F_2$ may be dielectrophoretic, electrophoretic, optical (as may arise, for example, through the use of optical tweezers), mechanical (as may arise, for example, from elastic traveling waves or from acoustic waves), or any other suitable type of force (or combination thereof). In one embodiment, forces $F_1$ and $F_2$ may be programmable. Using programmable forces, packets may be manipulated along arbitrarily chosen paths.

In the illustrated embodiment of FIG. 1, position sensor 23 may be operated with various mechanisms to sense positions of packets 21. For instance, an optical imaging system may be used to determine and monitor packet positions. Specifically, an optical microscope may be connected to a CCD imaging camera, which may be interfaced with an imaging card in a computer. The information from the imaging card may be processed in the computer using image-analysis software. Alternatively, a CCD imaging device may be incorporated in or above the reaction surface 12 to monitor the positions of packets. Thus, positions of packets and their movement on reaction surface 12 may be continuously monitored and recorded in the computer. A different mechanism of packet position sensing uses electrical impedance measurements. The presence or absence of a packet between two electrode elements may affect the electrical impedance between the electrodes. Thus, measurement of electrical impedance between electrode elements may allow for indirect monitoring of packet positions.

In order to better understand the operation and design of the currently disclosed method and apparatus, which will be discussed first in relation to dielectrophoretic forces, it is useful to discuss dielectrophoretic theory in some detail. Such a discussion is aided by FIG. 2, which illustrates two packets, 21a and 21b, both being subjected to dielectrophoretic forces.

Figure 2:
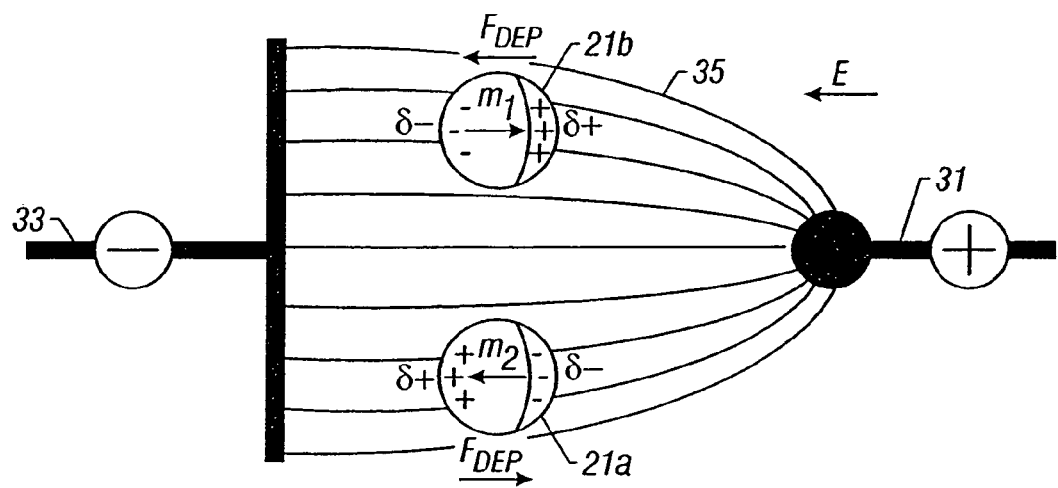
FIG. 2 is a simplified illustration of dielectrophoretic force phenomenon.

Dielectrophoretic forces may arise when a packet is placed in an inhomogeneous electrical field (AC or DC). In FIG. 2 the electrical field is weaker on the left side than on the right side. An electrical field induces electrical polarizations in the packet. The polarization charges are depicted at the two ends of the packets 21a and 21b along the field lines 35. Dielectrophoretic forces result from the interaction between the induced polarization (labeled as $m_1$ and $m_2$ in FIG. 2) and the applied inhomogeneous field. If a packet is suspended in a medium having different dielectric properties, such as a partitioning medium, then the packet may remain compartmentalized and may readily respond to manipulation forces against viscous drag. In a field of non-uniform strength, a packet may be directed towards either strong (packet 21a) or weak (packet 21b) electrical field regions, depending on whether the packet is more (packet 21a) or less (packet 21b) polarizable than a partitioning medium. In a field of non-uniform phase distribution (i.e. a traveling electrical field), a packet may be directed towards field regions of larger or smaller phase distribution, depending whether the packet has a longer or shorter dielectric response time than that of a partitioning medium.

DEP Theory

When a packet of radius r, suspended in an immiscible medium of different dielectric properties, is subjected to an electrical field of frequency f, the polarization of the packet can be represented using an effective dipole moment (Wang et al., "A Unified Theory of Dielectrophoresis and Traveling Wave Dielectrophoresis", Journal of Physics D: Applied Physics, Vol 27, pp. 1571-1574, 1994, incorporated herein by reference)

$$\vec{m}(f) = 4\pi \in_m r^3 P_{CM}(f) \vec{E}(f) \quad (1)$$

where $\vec{m}(f)$ and $\vec{E}(f)$ are the dipole moment and field vectors in the frequency domain, $P_{CM}(f)$ is the so-called Clausius-Mossotti factor, given by $$P_{CM}(f)=(\in_d{}^*-\in_m{}^*)/(\in_d{}^*+2\in_m{}^*). \quad (2)$$

Here $\in_k{}^*=\in_k-j\sigma_k/(2\pi f)$ are the complex permittivities of the packet material (k=d) and its suspension medium (k=m), and $\in$ and $\sigma$ refer to the dielectric permittivity and electrical conductivity, respectively. Using the effective dipole moment method, the DEP forces acting on the packet are given by $$\vec{F}(f)=2\pi r^3\in_m(Re[P(f)]\nabla E_{(rms)}{}^2+Im[P(f)](E_{xo}{}^2\nabla\phi_{xo}+E_{yo}{}^2\nabla\phi_{yo}+E_{zo}{}^2\nabla\phi_{zo})) \quad (3)$$

where E(rms) is the RMS value of the field strength, $E_{io}$ and $\phi_{io}$ (i=x; y; z) are the magnitude and phase, respectively, of the field components in a Cartesian coordinate frame. Equation (3) shows that the DEP force contains two independent terms. The first, relating to the real (in phase) part of the polarization factor Re[P(f)] and to non-uniformities in the field magnitude ($\nabla E_{(rms)}{}^2$). Depending on the sign of Re[P(f)], this force directs the packet either toward strong or weak field regions. The second term relates to the imaginary (out of phase) part of the polarization factor (Im[P(f)]) and to field phase non-uniformities ($\nabla\phi_{io}$, i=x; y; z) that correspond to the field traveling through space from large to small phase regions. Depending on the sign of Im[P(f)], this directs packets toward regions where the phase values of the field components are larger or smaller.

Equations (1-3) indicate that the DEP phenomena have the following characteristics:

(1) DEP forces experienced by packets are dependent on the dielectric properties of the packets ($\in_d{}^*$) and the partitioning medium ($\in_m{}^*$).

(2) The strong dependence of three-dimensional DEP forces on the field configuration allows for versatility in implementing dielectrophoretic manipulations.

DEP Forces on Packets

In one embodiment, a conventional dielectrophoresis component may be used for packet manipulation. In this case, the DEP force is given by $$\vec{F}(f)=2\pi r^3\in_m Re[P(f)]\nabla E_{(rms)}{}^2 \quad (4)$$

where r is the packet radius, $\in_m$ is the dielectric permittivity of the suspending fluid. Re[P(f)] is the real (in phase) part of the polarization factor and $\nabla E_{(rms)}{}^2$ is the field non-uniformity factor. For packets of water ($\in=78$ and $\sigma>10^{-4}$ S/m) suspended in a hydrocarbon fluid ($\in=\sim2$ and $\sigma\sim0$), the factor Re[P(f)] is always positive and close to unity. Therefore, water packets are always attracted towards regions of large field strength. For example, if an electrode array composed of circular electrodes arranged in a hexagonal fashion is provided, water packets may be dielectrophoretically moved towards and trapped between, for example, an electrode pair, over a single electrode, or above a plurality of electrodes to which electrical signals are applied. Switching the electrical signals may result in movement of the DEP traps and may cause water packets to move in a chamber. Thus, packet manipulation may be realized by switching electrical signals applied to an electrode array so that DEP field traps are made "mobile" within a chamber.

Typical Forces and Velocities

For a water packet of 100 µm suspended in a hydrocarbon fluid such as decane, the DEP force may be on the order of 1000 pN if the field non-uniformity is $1.25\times10^{13}$ V$^2$/m$^3$ (equivalent to 5V RMS applied to an electrode pair of distance 50 µm with the field decaying to zero at 1000 µm). If the viscosity of the hydrocarbon fluid is small (0.838 mPa for Decane), the packet velocity may be of the order of 600 µm/sec, indicating that fast manipulation of packets is possible with electrode arrays. In the above analysis, DEP force equation (4) has been used, which was developed for non-deformable particles and holds well for suspended particles (such as cells, latex particles). Fluid packets may be deformed under the influence of applied electrical field, affecting the accuracy of equation (4) in describing DEP forces for packets. Nevertheless, equation (4) should be generally applicable with some possible correction factors for different packet shapes.

Figure 3:
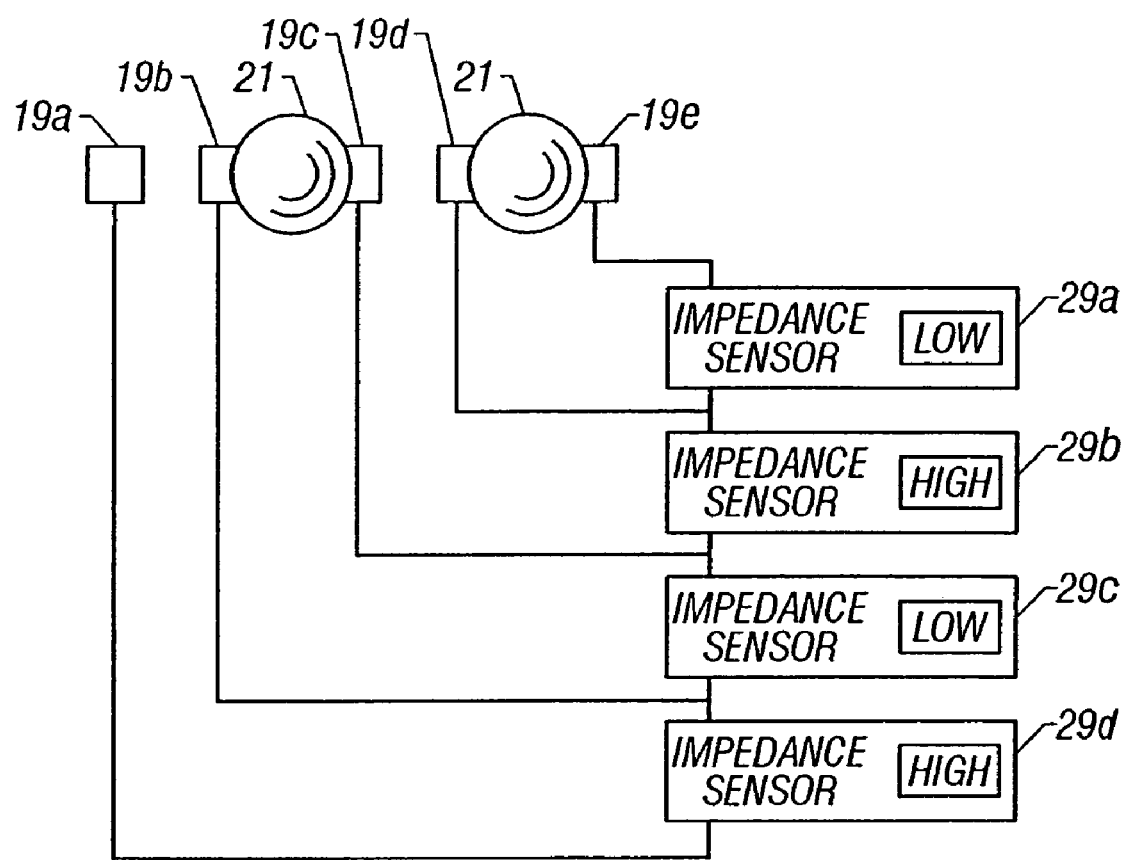
FIG. 3 illustrates a position sensing system according to one embodiment of the presently disclosed method and apparatus.

FIG. 3 shows one possible implementation of position sensor 23 of FIG. 2. Shown in FIG. 3 are five impedance sensing electrodes 19, here illustrated as 19a, 19b, 19c, 19d, and 19e. Each sensing electrode 19 may be coupled to an impedance sensor 29, here illustrated as impedance sensors 29a, 29b, 29c, and 29d. In one embodiment, impedance sensing electrodes 19 may be positioned in operative relationship with surface 12 of fluidic device 10 in FIG. 1. For instance, sensing electrodes 19 may be placed on or near surface 12. As packets 21 are manipulated about surface 12 by the application of appropriate manipulation forces, impedance sensing electrodes 19 and sensors 29 may sense a position of packets 21 by making one or more impedance measurements.

If the dielectric medium above an electrode is displaced by a packet having different dielectric and/or conductive properties, the impedance detected at the electrode element will change. Thus, one may determine the position of packets 21 by noting the impedance measurements associated therewith. As is shown in FIG. 3, the impedance between impedance sensing electrodes 19a and 19b is "high" (see impedance sensor 29d) relative to, for instance, the impedance between impedance sensing electrodes 19b and 19c (see impedance sensor 29c). Thus, by pre-determining that the "high" impedance value corresponds to the impedance due to the partitioning medium, it may be deduced that some material of different impedance to the partitioning medium lies somewhere between impedance sensing electrodes 19d and 19e and between 19b and 19c because the impedance associated with those electrodes is "low" (see impedance sensor 29a). By like reasoning, one may assume that no packet lies between impedance sensing electrodes 19c and 19d, for the impedance between those two electrodes is relatively "high" (see impedance sensor 29b and 29c).

Those of skill in the art will appreciate that the "low" and "high" values discussed above may be reversed, depending upon the relative impedances of a packet and of a suspending medium. In other words, in some situations, a relatively "high" impedance measurement may signal the presence of a packet in between a pair of electrodes while a relatively "low" impedance may signal the lack of a packet. Those of skill in the art will also appreciate that individual impedance measurements may exhibit a wide range of values (not just "low" or "high"), and it may be possible to characterize different types and sizes of materials by noting their associated impedance measurements. For instance, one may be able to differentiate, by type, the two packets 21 of FIG. 3 by noting any differences in their impedance readings on impedance sensors 29a and 29c.

Impedance sensing may be based on the so-called mixture theory, which associates the impedance of a heterogeneous system with the dielectric properties of various system components and their volume fractions. Take a two-component, heterogeneous system where component 2 having complex dielectric permittivity $$\left(\varepsilon_2^* = \varepsilon_2 - j\frac{\sigma_2}{2\pi f}, f \text{ is the frequency}\right)$$

and a volume fraction α is suspended in component 1 having complex dielectric permittivity $$\left(\varepsilon_1^* = \varepsilon_1 - j\frac{\sigma_1}{2\pi f}\right).$$

The complex permittivity of the total system is given by (Wang et al., "Theoretical and experimental investigations of the interdependence of the dielectric, dielectrophoretic and electrorotational behavior of colloidal particles" in J. Phys. D: Appl. Phys. 26: 312-322, 1993, incorporated herein by reference)

$$\varepsilon_{sys}^* = \varepsilon_1^* \frac{\frac{1}{\alpha} + 2\frac{\varepsilon_2^* - \varepsilon_1^*}{\varepsilon_2^* + 2\varepsilon_1^*}}{\frac{1}{\alpha} - \frac{\varepsilon_2^* - \varepsilon_1^*}{\varepsilon_2^* + 2\varepsilon_1^*}}.$$

The total impedance of the system, which is assumed to have length L and cross-sectional area A, is given by $$\Omega = \frac{L}{\omega \varepsilon_{sys}^* A}.$$

The electrical impedance between two electrode elements in the presence or absence of a packet may be analyzed using the above equations, with the parameters L and A determined experimentally. The existence of a packet may correspond to α>0 and the absence of a packet may correspond to α=0. From these equations, an impedance change would occur when a packet having different dielectric property ($\varepsilon_2^*$) from the partitioning media ($\varepsilon_1^*$) is introduced into the space between the two electrode elements.

A relatively low impedance measurement may indicate an obstruction or a packet (as is illustrated in FIG. 3) on or near surface 12. By determining impedance values, one may map locations of obstructions or packets relative to surface 12. In this way, one may generate a packet and/or obstruction distribution map with respect to reaction surface 12 of fluidic device 10. With the benefit of this disclosure, one of skill in the art will appreciate that the description associated with FIG. 3 may be implemented in many different ways. In particular, one may use any suitable type of impedance measurement devices known in the art to function with one or more electrodes. Such devices may include an impedance analyzer, a DC/AC conductance meter, or any circuit based upon methods of operation of these or other instruments having similar function.

Figure 4:
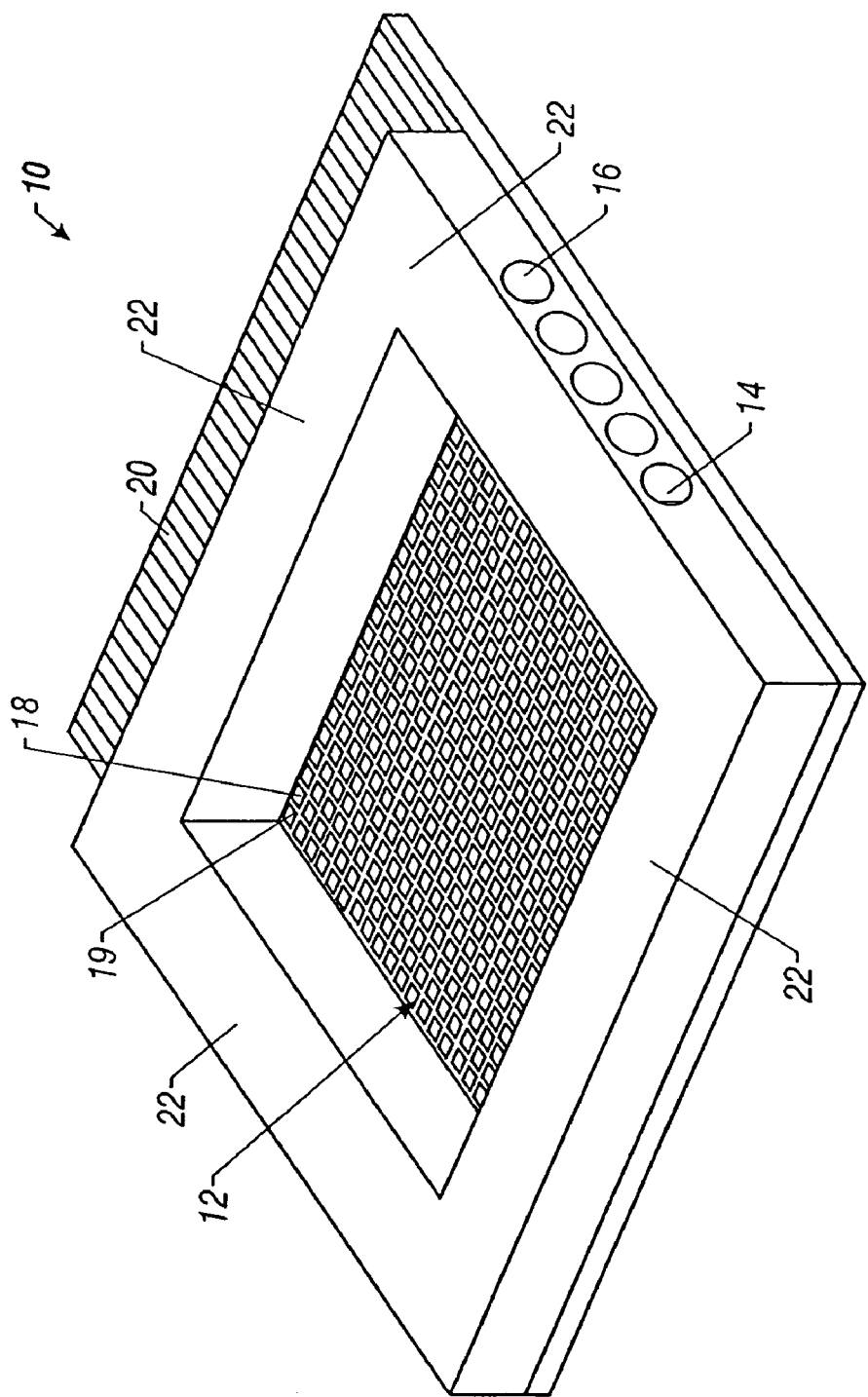
FIG. 4 is a three dimensional view of a microfluidic device according to one embodiment of the presently disclosed method and apparatus.

FIG. 4 shows a three dimensional view of one embodiment of a fluidic device 10 according to the present disclosure. Fluidic device 10 includes reaction surface 12, an inlet port 14, an outlet port 16, driving electrodes 18, impedance sensing electrodes 19, connectors 20, and wall 22.

Reaction surface 12 provides an interaction site for packets. In one embodiment, reaction surface 12 may be completely or partially covered with a partitioning medium (not shown in FIG. 4) or other substance. In one embodiment, reaction surface 12 may be coated. In particular, for manipulation of aqueous packets in a hydrophobic partitioning medium, reaction surface 12 may include a hydrophobic coating, or layer, having a hydrophobicity similar to or greater than the hydrophobicity of the partitioning medium. Such a coating may prevent an aqueous packet from sticking, from spreading, or from becoming unstable upon contact with reaction surface 12. Additionally, a coating may modify association and/or interaction forces between packets and reaction surfaces to facilitate manipulation of packets by appropriate manipulation forces. Further, a coating may be used to reduce contamination of reaction surfaces by reagents in packets. Still further, a coating may facilitate the deliberate adhesion, wetting, or sensing of packets at or on reaction surfaces. If a dielectric layer coating is applied, the layer should be made sufficiently thin to allow AC electric field penetration through the dielectric layer. In one embodiment, the thickness of the layer may be between about 2 nm and about 1 micron. In one embodiment, a hydrophobic coating may be Teflon that may be applied by means known in the art such as sputtering or spin-coating. It is to be understood that any other suitable coating that modifies an interaction between packets and the reaction surface may be used.

Reaction surface 12 may be formed from a number of suitable materials. In the illustrated embodiment, reaction surface 12 is a planar surface that has an upper surface including driving electrodes 18 and impedance sensing electrodes 19. Although illustrated as being coplanar with reaction surface 12, it is to be understood that driving electrodes 18 and 19 may also be elevated or depressed with respect to reaction surface 12. Likewise, reaction surface 12 need not be planar. Rather, it may have concave or convex portions, or it may be deformed in some other manner. Reaction surface 12 may be glass, silicon dioxide, a polymer, a ceramic, or any suitable electrically insulating material. The dimensions of reaction surface 12 may vary widely depending on the application but may be between about 20 microns by about 20 microns and about 50 centimeters by about 50 centimeters. More particularly, reaction surface 12 may be between about 3 millimeters by about 3 millimeters and about 30 centimeters by about 30 centimeters.

Inlet port 14 may be adapted to inject or introduce materials onto reaction surface 12 and may be any structure allowing ingress to reaction surface 12. In the illustrated embodiment, inlet port 14 consists of an opening in wall 22. Such an opening may be of any suitable size or shape. Alternatively, inlet port 14 may be a syringe needle a micropipette, a tube, an inkjet injector, or any other suitable device able to inject a material for introduction onto reaction surface 12. Using a micropipette or equivalent device, wall 22 may not need to include any openings. Rather, material may be introduced onto reaction surface 12 from above. A micropipette or any other equivalent device may be attached to a micromanipulation stage (not shown in FIG. 4) so that material may be precisely deposited onto specific locations of reaction surface 12. In one embodiment, inlet port 14 may consist of a cylindrical tube opening onto reaction surface 12. Such a tube may have a diameter of between about 1 micrometer and about 1 mm and, more particularly, between about 10 and 100 microns.

Outlet port 16 may be adapted to collect packets of material from reaction surface 12. Outlet port 16 may be any structure allowing egress from reaction surface 12. In the illustrated embodiment, outlet port 16 consists of an opening in wall 22. The opening may be of any suitable size or shape. Alternatively, outlet port 16 may be a micropipette or any other equivalent device able to collect a material from reaction surface 12. Wall 22 may not need to include any openings. Rather, packets of material may be collected from reaction surface 12 from above. A syringe or any other equivalent device may be attached to a micromanipulation stage (not shown in FIG. 4) so that packets may be precisely collected from specific locations on reaction surface 12. In one embodiment, outlet port 16 may consist of a cylindrical tube opening onto reaction surface 12. Such a tube may have a diameter of about 1 millimeter and a length of about 3 centimeters or longer.

In one embodiment, inlet port 14 and outlet port 16 may be integral. For instance, in the embodiment shown in FIG. 1 port 15 is a cylindrical tube opening onto reaction surface 12. In alternative embodiments, one micropipette may serve as both an inlet port and an outlet port. Alternatively, a single opening in wall 22 may serve both input and output functions. In another embodiment, multiple inlet and outlet ports may be utilized.

Fluidic device 10 may include an arbitrary number of inlet and outlet ports. For example, any one of the three unnumbered openings in wall 22, illustrated in FIG. 4, may serve as an inlet port, an outlet port, or an integral inlet-outlet port, such as port 15 of FIG. 1. In another embodiment, multiple inlet and/or outlet ports may extend completely or partially along a wall 22 so that materials may be introduced and/or collected to and/or from reaction surface 12. In such an embodiment, one may more precisely introduce or collect materials.

In FIG. 4, driving electrode 18 is one of a number of other driving electrodes arranged in an array upon reaction surface 12. In this embodiment, driving electrodes 18 may be associated with force generator 25 of FIG. 1, for the driving electrodes 18 may contribute to the generation of forces, such as forces $F_1$ and $F_2$ of FIG. 1, to manipulate packets of material on reaction surface 12 to promote, for instance, microfluidic interactions.

Dielectrophoretic forces may be generated by an array of individual driving electrodes 18 fabricated on an upper surface of a reaction surface 12. The driving electrode elements 18 may be individually addressable with AC or DC electrical signals. Applying an appropriate signal to driving electrode 18 sets up an electrical field that generates a dielectrophoretic force that acts upon a packet, known to be at a certain location through impedance measurements as described above in relation to FIG. 3. Switching different signals to different electrodes sets up electrical field distributions within fluidic device 10. Such electrical field distributions may be utilized to manipulate packets in a partitioning medium.

In particular, the movement of packets under the influence of a manipulation force may be controlled by switching appropriate electrical signals to different combinations of driving electrodes 18. Specifically, the switching of electrical signals may initiate different field distributions and generate manipulation forces that trap, repel, transport, or perform other manipulations upon packets of material. By programmably switching electrical signals to different combinations of driving electrodes 18 within an array, electric field distributions and manipulation forces acting upon packets may be programmable so that packets may be manipulated along arbitrarily chosen or predetermined paths in a partitioning medium along reaction surface 12. Thus, packets may be manipulated in an unlimited manner. Signals may be appropriately switched to cause, for instance, a packet to move a single "unit distance"—a distance between two neighboring electrodes. Further, by programmably switching electrical signals, different microfluidic reactions may be performed in series or in parallel. An electrode array having such an ability to utilize programmable dielectrophoretic forces by programmed switching of electrical signals to different combinations of driving electrodes 18 may be termed a programmable dielectrophoretic array (PDA).

In FIG. 4, impedance sensing electrode 19 is one of a number of other impedance sensing electrodes arranged in an array upon reaction surface 12. In this embodiment, impedance sensing electrodes 19 may be associated with position sensor 23 of FIG. 1 and is illustrated in FIG. 3. Impedance sensing electrodes 19 contribute to the sensing of packet positions upon reaction surface 12 so that those packets of material may be monitored and manipulated according to position.

In the illustrated embodiment, driving electrodes 18 and impedance sensing electrodes 19 are electrodes of a two dimensional electrode array coupled to a top surface of reaction surface 12. The size of the array may vary according to need, but in one embodiment a 16 by 16 array is employed. Because fluidic device 10 is scaleable, smaller or larger arrays may be fabricated without significant departure from the present disclosure. For example, 256 by 256 arrays or larger may be made according to the present disclosure. Driving electrodes 18 and impedance sensing electrodes 19 within an array may be uniformly or non-uniformly spaced. The spacing may vary widely, but in one embodiment, the spacing may be between about 2 microns and about 200 microns. The electrodes may have different forms such as lines, squares, circles, diamonds, polygons, or other suitable shapes. The dimensions of each electrode may vary, but a typical electrode may be between about 0.2 microns and about 10 mm., and more particularly, between about 1 micron and about 200 microns. Driving electrodes 18 and impedance sensing electrodes 19 may be formed using any method known in the art. In one embodiment, such electrodes may be formed using standard photolithography techniques. For example, one may refer to, e.g., D. Qin et al, "Microfabrication, Microstructures and Microsystems", Microsystem Technology in Chemistry and Life Sciences (Ed. Manz and Becker), Springer, Berlin, 1997, pp 1-20, which is incorporated is herein by reference. Also, one may refer to Madou, Fundamentals of Microfabrication, CRC Press, Boca Raton, 1997, which is incorporated herein by reference. Depending upon the particular application, and the nature of the packets and partitioning medium, the size and spacing of electrodes 18 and 19 may be smaller than, of similar size, or larger than the diameters of the packets.

In one embodiment, impedance sensing electrodes 19 may be integral with driving electrodes 18. In such an embodiment, the resulting array may be termed an integral array. With an integral array, a single conductor coupled to reaction surface 12 may serve both purposes—driving packets and sensing positions of packets. Thus, a programmable manipulation force may be generated upon packets upon reaction surface 12 and a position of those packets may be sensed with a single electrode array.

In the embodiment of FIG. 4, wall 22 is adapted to enclose one or more sides of reaction surface 12. It is to be understood that wall 22 may be any suitable structure capable of enclosing one or more sides and/or the top of reaction surface 12. As illustrated, wall 22 encloses four sides of reaction surface 12, defining an open reaction surface chamber. In a most typical embodiment, the chamber may have a thickness of between about 16 microns and about 20 millimeters. In another embodiment, wall 22 may enclose the top of reaction surface 12, forming a closed reaction chamber.

Wall 22 may be formed from any suitable material. In one embodiment, wall 22 may be made from machined plastic, aluminum, glass, plastic, ceramic, or any combination thereof. In one embodiment, wall 22 may be partially or completely transparent to certain wavelengths of radiation. Thus, radiation may be transmitted through wall 22 to initiate or maintain certain microfluidic reactions or processes for sensing. For instance, a photochemical reaction may be initiated through wall 22.

Connectors 20 of FIG. 4 may be adapted to provide electrical connections to driving electrodes 18 and to impedance sensing electrodes 19. Connectors 20 may provide electrical connections to an entire array of electrodes, or to preselected ones or groups. In one embodiment, connectors 20 are coupled to a controller (not shown in FIG. 4) that may adjust a programmable manipulation force distribution generated by driving electrodes 18 according one or more packets position sensed with impedance sensing electrodes 19. Thus, such a controller may effectively provide a feedback mechanism between the driving electrodes 18 and the impedance sensing electrodes 19—The signals applied to driving electrodes 18 may be adjusted in view of one or more results from the impedance sensing electrodes 19.

Figure 5:
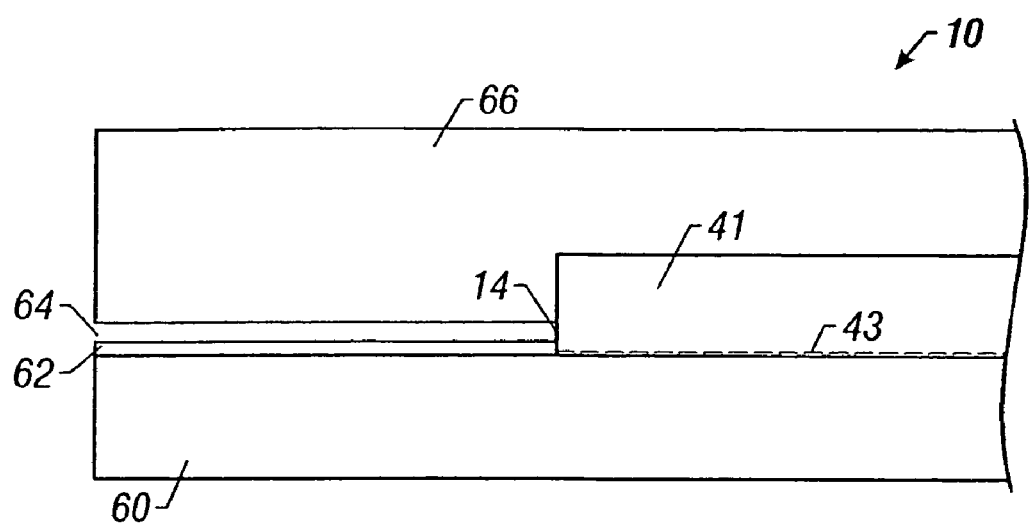
FIG. 5 is a side cross sectional view of a microfluidic device according to one embodiment of the presently disclosed method and apparatus.

Turning now to FIG. 5, there is shown a side cross section view of a fluidic device 10 according to the present disclosure. Fluidic device 10 includes a reaction chamber 41 and an array of integral impedance sensing and driving electrodes, integral array 43. In the illustrated embodiment, a control chip 60 is coupled to integral array 43. Positioned upon a top surface of control chip 60 may be capillary wall 62 that forms a lower surface of a capillary 64. Capillary 64 may lead to an inlet port 14 that leads into chamber 41. Although illustrated with only one inlet port, it is contemplated that there may be several such ports providing access to chamber 41. Above capillary 64 is a substrate 66 that, in one embodiment, is made of glass although any suitable material known in the art may be utilized instead.

In one embodiment, control chip 60 may be an integrated circuit configured to control integrated array 43. Alternatively, control chip 60 may be a control interface leading to another controlling device such as an integrated circuit, computer, or similar device that may control integral array 43. Control chip 60 may utilize flip-chip technology or any other suitable technique to establish electrical control over integral array 43 by switching different signals to and from it.

Figure 6:
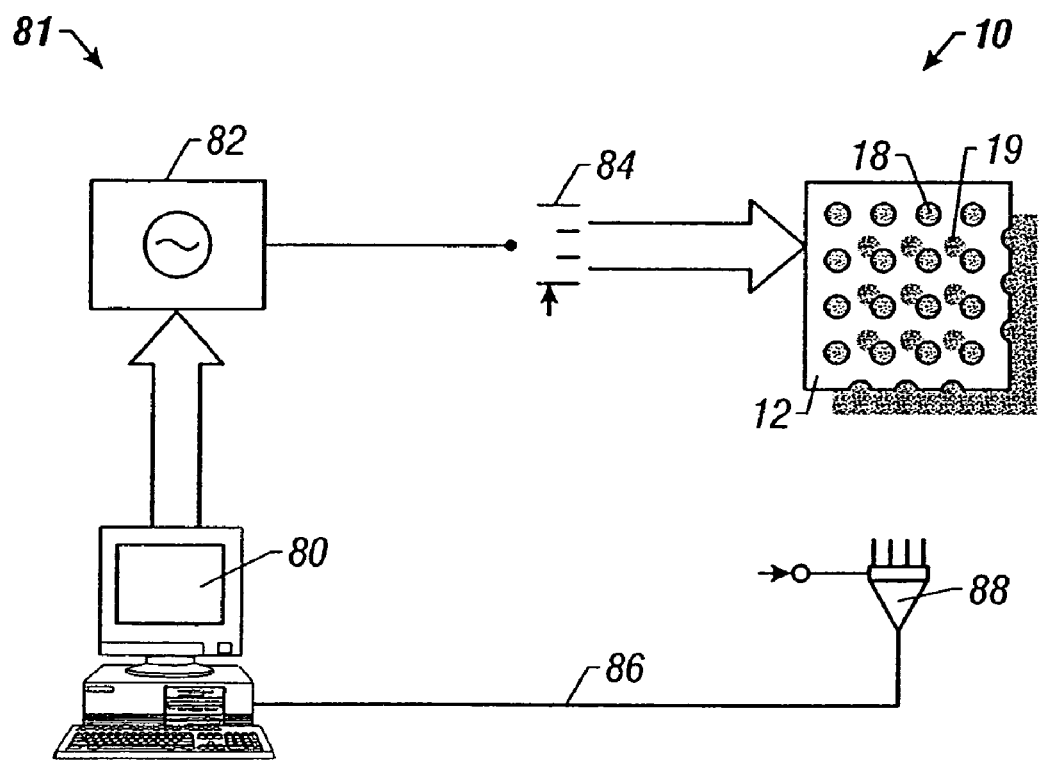
FIG. 6 is a simplified block representation of a microfluidic system according to one embodiment of the presently disclosed method and apparatus.

FIG. 6 shows a controller 81 according to one embodiment of the presently disclosed method and apparatus. Controller 81 may include a computer 80, a signal generator 82, an electrode selector 84, a transducer 88, and a fluidic device 10 having a driving electrode 18 and an impedance sensing electrode 19.

Computer 80 may be configured to control fluidic device 10 and the fluid processing occurring upon reaction surface 12. Computer 80 may have a user interface that allows for simple programming of signal generator 82 and transducer 88, which measures impedance, to allow for programmable microfluidic processing. In particular, computer 80 may programmably control the initiation/termination of one or more signals from signal generator 82, the parameters of the one or more signals including frequencies, voltages, and particular waveforms, and control the switching of one or more signals from generator 82 to different combinations of electrodes 18 and 19.

Computer 80 may vary signals in many ways. For instance, one signal having a first frequency component may be sent through electrode selector 84 to a driving electrode 18 while another signal having a second, different frequency component may be sent to, for instance, an impedance sensing electrode 19 and through electrode selector 84. Any sequence of signals or combinations of signals may be sent different combinations of electrodes and from the fluidic device 10. Any signal parameter may be varied and any electrode selection may be controlled so that appropriate electric fields may be established at particular locations upon reaction surface 12. Alternating Current or Direct Current signals may be utilized.

Signal generator 82 may send a driving signal to one or more driving electrodes 18 while sending a sensing signal to one or more impedance sensing electrodes 19. In one embodiment, the driving signal and the sensing signal may comprise a single, composite processing signal having different frequency components. Such a signal may be used with an integrated array to provide (via a single processing signal) a frequency component to generate a programmable manipulation force and a frequency component to provide an impedance sensing signal. The manipulation and impedance sensing components may also be combined by multiplexing or switching in time as is known in the art.

In one embodiment, signal generator 82 provides one or more programmable driving signals to one or more driving electrodes 18 through electrode selector 84 so that a programmable alternating-current electric field, such as a non-uniform field, may be produced at reaction surface 12. That electric field may induce polarization of packets of materials adjacent to or in the vicinity of the one or more driving electrodes 18. A programmable dielectrophoretic force distribution may, in this manner, be generated that manipulates packets in a controllable, programmable manner so that varied programmable fluidic interactions may take place upon reaction surface 12.

In one embodiment, signal generator 82 provides a sensing signal to one or more impedance sensing electrodes 19 so that an impedance measurement may be made. The impedance sensing signal may be applied to one or more pairs of impedance sensing electrodes 19 and a change in voltage or current may be detected and transmitted to computer 80 via sensing electrodes 88 and wire 86. Computer 80 may then compute the impedance and hence, determine whether a packet or obstruction was present at or near the pair(s) of impedance sensing electrodes 19 being probed.

In an embodiment utilizing a single integrated array (instead of separate impedance sensing and driving electrode arrays, an integrated array utilizes electrodes that function to both drive and sense packets), the integrated array may both generate a programmable manipulation force and sense an impedance. In one approach, electrical sensing signals for sensing electrode impedance may be applied at different frequencies from driving signals for manipulation of packets. Summing signal amplifiers (not shown) may be used to combine signals from sensing and driving electronics. By using a frequency filter network (not shown), electrode impedance sensing signals may be isolated from the driving signals. For example, a constant current at sensing frequency $f_s$ may be applied to integrated electrode pairs to be measured. The sensing electronics 88, may then be operated at only the applied frequency $f_s$ to determine a voltage drops across the integrated electrode pairs, thus allowing the impedance at the sensing frequency $f_s$ to be derived without interference from the driving signals.

In another embodiment, driving signals may be used to monitor electrical impedance directly. Driving signals may be switched to one or more integrated electrodes to generate a force to manipulate or interact packets upon a reaction surface. Simultaneously, an electrical current sensing circuit may be used to measure electrical current going through the energized integrated electrodes. Electrode impedances may be derived from such measurements of electrical current.

Although any suitable device may be used, in one embodiment a function generator is used as signal generator 82. More particularly, an arbitrary waveform signal generator in combination with voltage or power amplifies or a transformer may be used to generate the required voltages. In one embodiment, signal generator 82 may provide sine-wave signals having a frequency up to the range of GHz and more particularly between about 1 kHz and about 10 MHz and a voltage between about 1 V peak-to-peak and about 1000 V peak-to-peak, and more particularly, between about 10 V peak-to-peak and about 100 V peak-to-peak.

As illustrated, signal generator 82 may be connected to an electrode selector 84. Electrode selector 84 may apply one or more signals from signal generator 82 to one or more individual electrodes (impedance sensing electrodes and/or driving electrodes may be individually addressable). Electrode selector 84 may be one of a number of suitable devices including a switch, a multiplexer, or the like. Alternatively, electrode selector 84 may apply one or more signals to one or more groups of electrodes. In one embodiment, selector 84 is made of electronic switches or a multiplexer. Selector 84 may be digitally controlled. With the benefit of this disclosure, those of skill in the art will understand that selector 84 may be any suitable device that may programmably divert one or more signals to one or more electrodes in any arbitrary manner.

As illustrated in FIG. 6, controller 81 provides a feedback loop mechanism from impedance sensing electrodes 19 to driving electrodes 18 via computer 80, which itself is coupled to signal generator 82, selector 84, and transducer 88. With the benefit of the present disclosure, those of skill in the art will recognize that controller 81 may contain more or fewer components. The feedback mechanism allows computer 80 to tailor its commands to signal generator 82 according to positions of packets upon reaction surface 12, as determined by impedance sensing electrodes 19. Thus, controller 81 allows for the adjustment of driving signals (and hence the adjustment of programmable manipulation forces) according to positions of packets (as determined by impedance sensing electrodes 19). In embodiments utilizing an integral array of electrodes having integral impedance sensing electrodes 19 and driving electrodes 18, a feedback mechanism may operate as follows. Positions of packets may be determined by measuring impedances between electrical elements by applying impedance sensing signals to the integral array. Position information may then be used to control driving signals to the integral array to perform microfluidic processing through the manipulation of packets. In one embodiment computer 80 may be replaced by an application specific integrated circuit controller (ASIC) designed specifically for the purpose.

Figure 7:
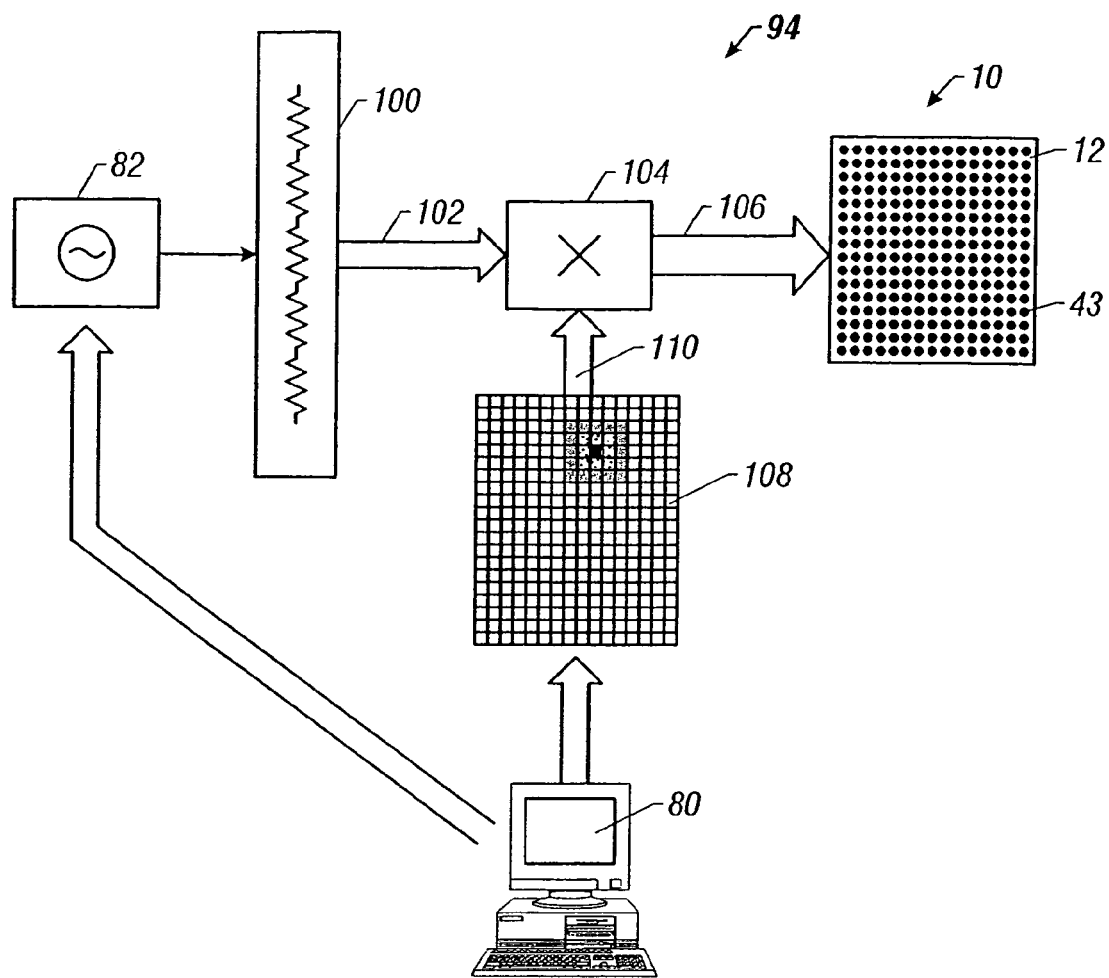
FIG. 7 is a simplified block representation of a signal application arrangement according to one embodiment of the presently disclosed method and apparatus.

FIG. 7 shows an electrode driver 94 according to an embodiment of the presently disclosed method and apparatus. Driver 94 includes a computer 80, a signal generator 82, a resistor network 100, a switching network 104, and a bitmap 108. Driver 94 is coupled to fluidic device 10 which includes reaction surface 12 and an integral array 43.

Driver 94 may assist in the application of signals to integral array 43 in order to direct microfluidic interactions of packets of material upon reaction surface 12. In one embodiment, computer 80 directs signal generator 82 to apply an AC signal to integral array 43. In the illustrated embodiment, from signal generator 82 there may be provided, for example, eight increasing voltage amplitudes using resistor network 100, although more or fewer voltage amplitudes may be used. The eight AC signals may be distributed by switching network 104 via connection 106 to the integral array 43 according to a bitmap 108 or according to any other suitable data structure stored in computer 80 or in another device. By modifying bitmap 108 via computer 80, different voltage amplitudes may be applied to different electrodes.

In one embodiment, signals to each electrode of integral array 43 may be represented in bitmap 108 by 3 bits to address eight available voltage amplitudes. Voltage amplitude distributions of bitmap 108 may be transmitted sequentially to switching network 104 via connection 110 twelve bits at a time using a communication protocol as is known in the art. In one embodiment, the communication protocol may use the following convention. To address a single electrode of integral array 43, the first four bits may specify the row of the array. The second four bits may specify the column of the array. The next three bits may specify the desired voltage to be applied. The last bit may be used for error control by parity check. The rows/column arrangement may be used for different layouts of arrays. For instance, the row/column convention of addressing may be used even for a hexagonal grid array configuration. Those skilled in the art will appreciate that other methods may be used to address the electronic switching network 104 from computer 80.

Figure 8:
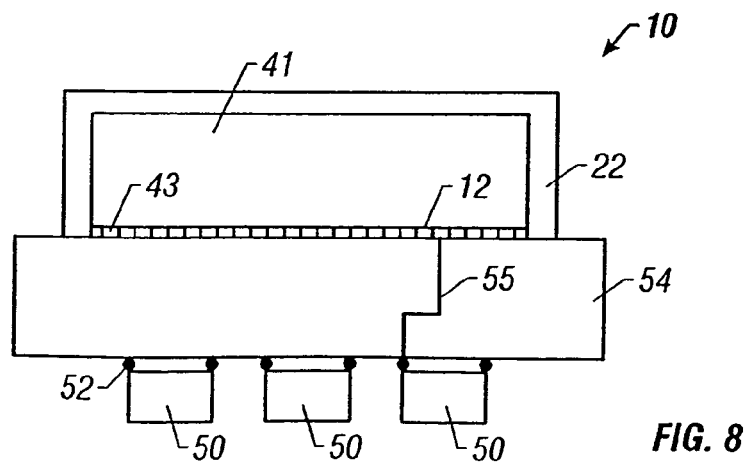
FIG. 8 is a cross sectional view of microfluidic device according to one embodiment of the presently disclosed method and apparatus.

FIG. 8 is side cross-section view of one embodiment of a fluidic device 10. Fluidic device 10 includes a wall 22 which encloses the sides and top of a reaction surface 12 to form a reaction chamber 41. Reaction surface 12 includes an integral array 43. Coupled to the integral array may be an interface board 54. Interface board 54 may interface the integral array 43 with integrated circuits 50 via interconnect 55 and solder bumps 52.

In the embodiment of FIG. 8, interface board 54 may be sandwiched between chamber 41 and integrated circuits 50. On one side, interface board 54 may provide electrical signals (AC or DC) to electrodes of integral array 43, while the other side of interface board 54 may include pads for flip-chip mounting of integrated circuits 50. Intermediate layers of interface board 54 may contain electrical leads, interconnects and vias, such as interconnect 55 to transfer power and signals to and from electrodes of integral array 43 and integrated circuits 50.

Interface board 54 may be fabricated using suitable PC-board and flip chip technologies as is known in the art. Suitable silk-screened or electroplated flip-chip solder bump techniques may likewise be used. Alternatively, ink-jet solder deposition may be used as is known in the art.

Figure 9:
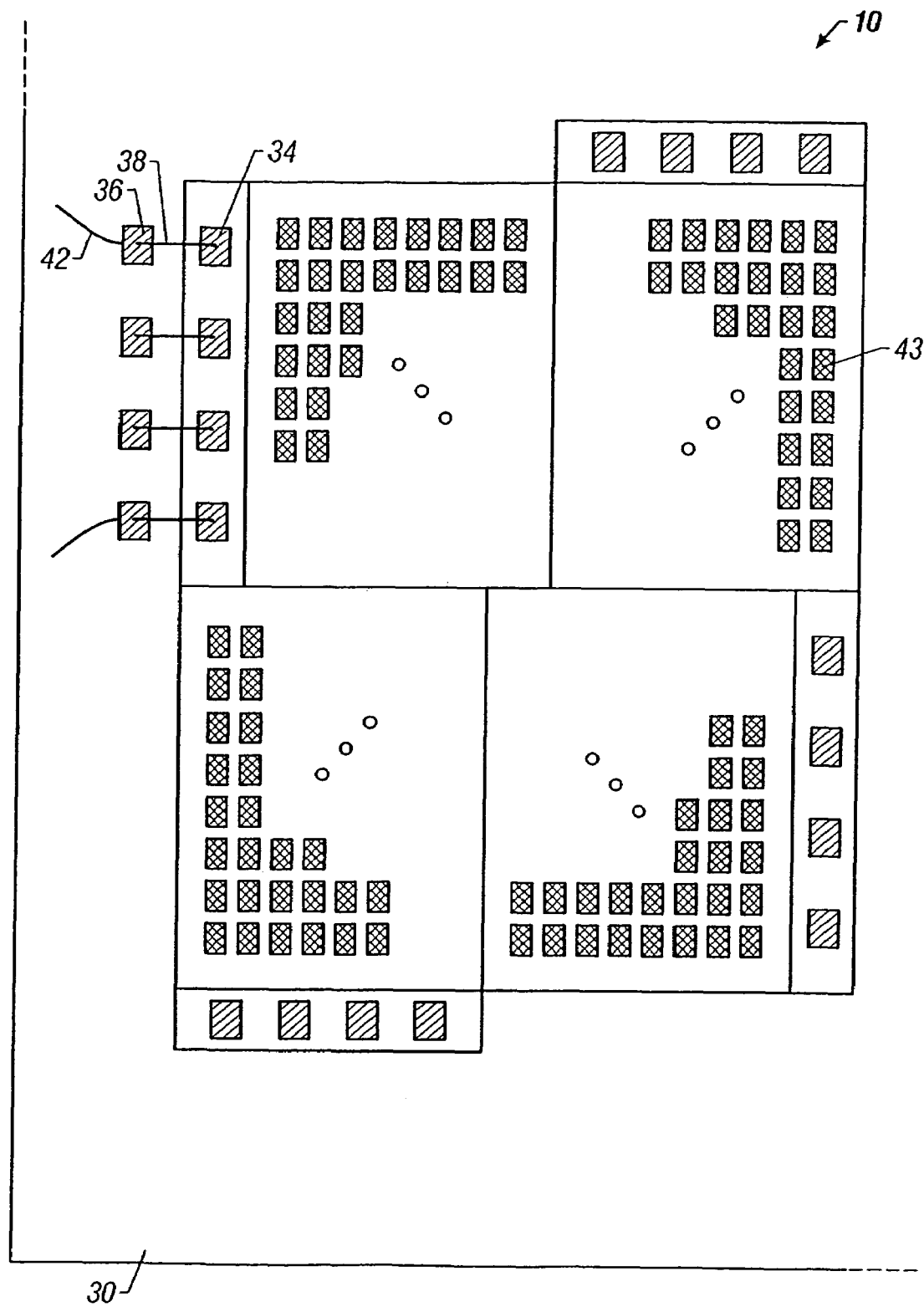
FIG. 9 is a top view of a microfluidic device according to one embodiment of the presently disclosed method and apparatus.

FIG. 9 is a top view of an embodiment of a fluidic device 10. In the illustrated embodiment, fluidic device 10 is made up of four distinct 8 by 8 integral arrays 43, forming a 16 by 16 array. Under each 8 by 8 array may be situated an integrated circuit (not shown in FIG. 9) that may provide control and signal processing to electrodes of the integral array 43. The integral arrays may be coupled to a circuit conducting pad 34 that may be coupled to an interface conducting pad 36 by a bond wire 38 (shown only in one quadrant). Connected to interface conducting pad 36 may be wire 42, or another suitable connector such as a PC board connector, leading to a computer or other suitable controlling device.

Figure 9B:
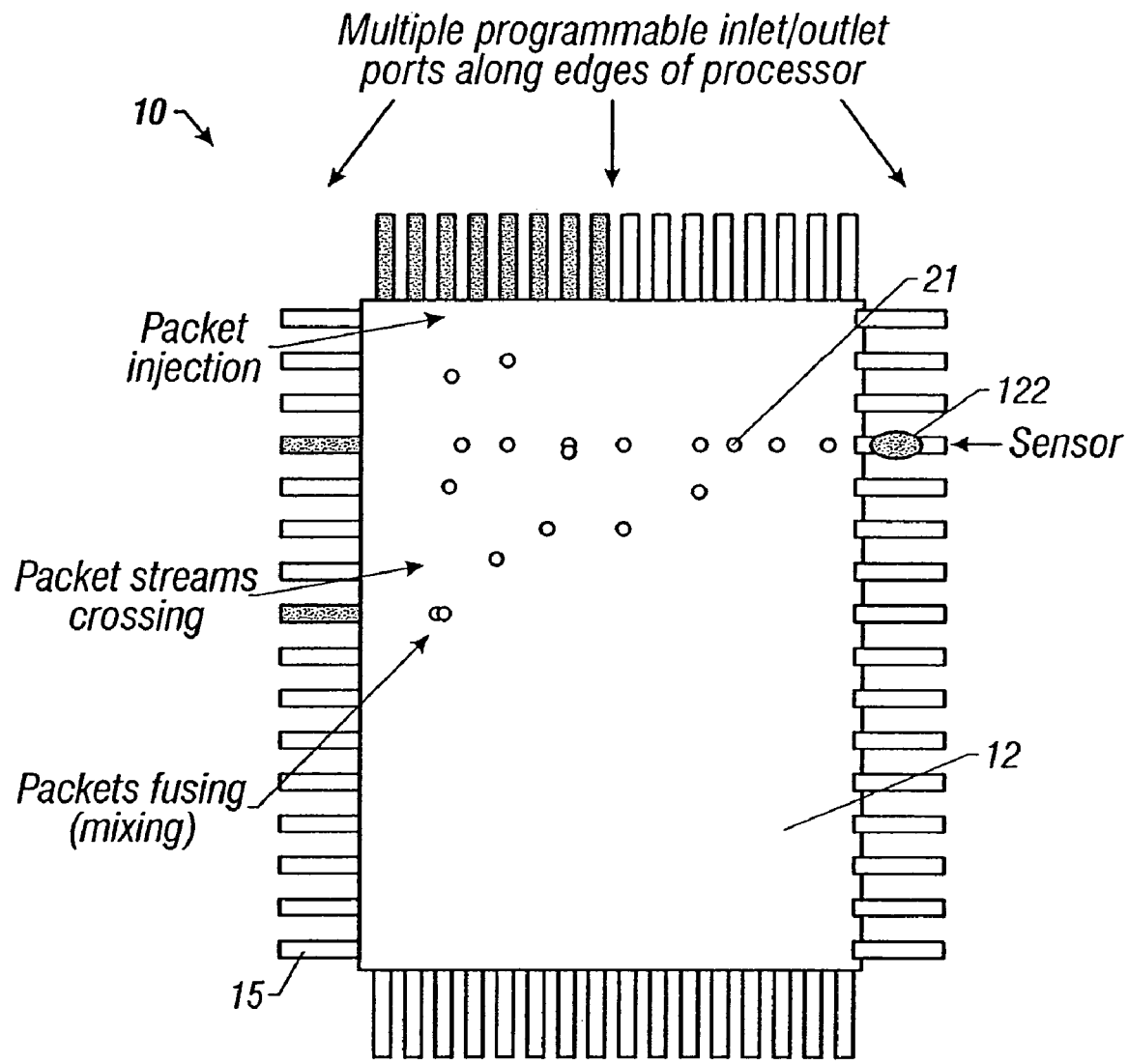
FIG. 9B is another top view of a microfluidic device according to one embodiment of the presently disclosed method and apparatus.

FIG. 9B is another top view of an embodiment of a fluidic device 10. In this embodiment, many ports 15 are situated along edges of fluidic device 10. These ports 15 may serve to inject and/or collect packets 21 to/from reaction surface 12. Also illustrated is a sensor 122 positioned adjacent a port 15. Such a sensor is described in reference to FIG. 10 below.

Figure 10:
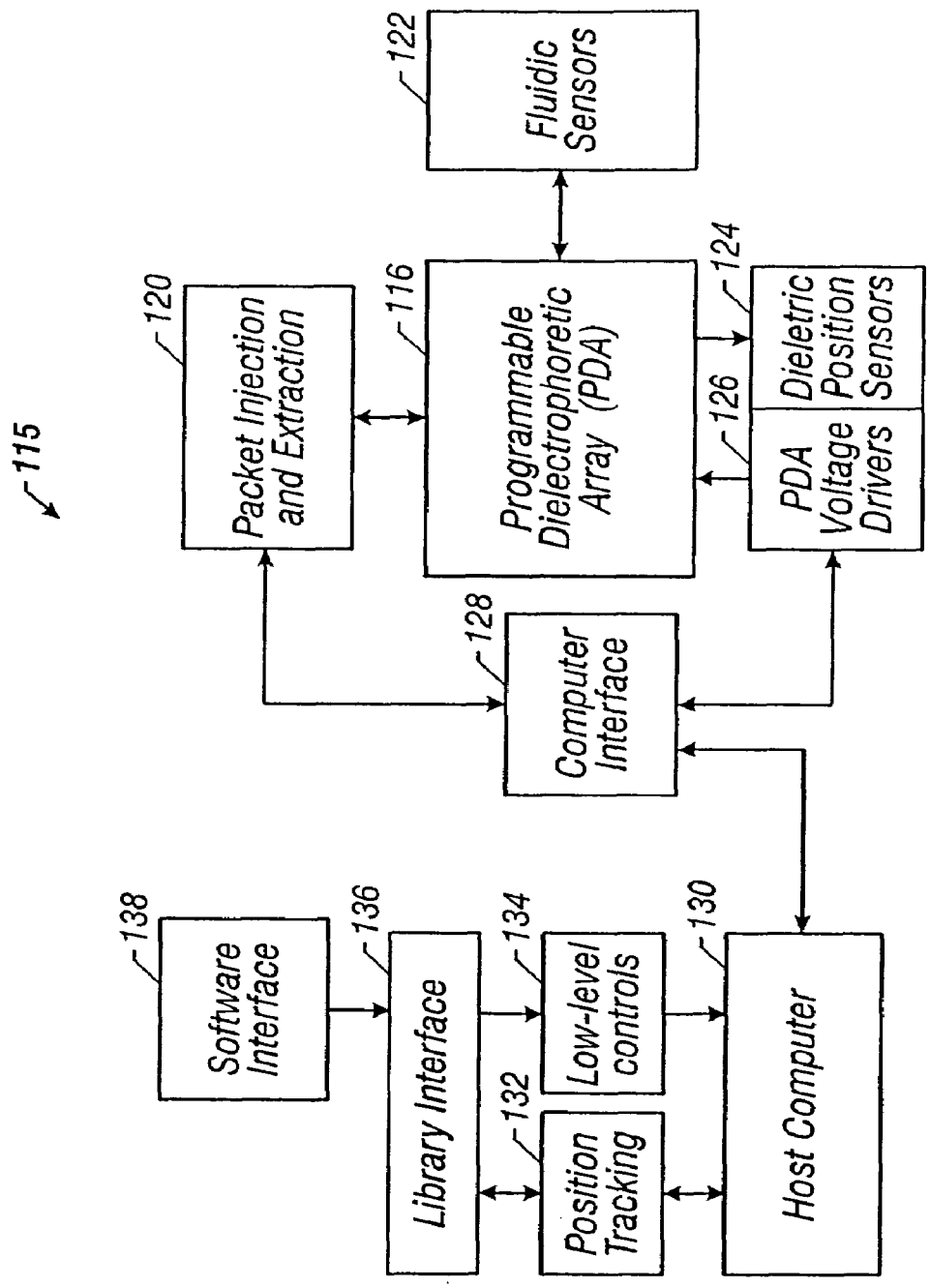
FIG. 10 is a simplified block representation of a microfluidic system according to one embodiment of the presently disclosed method and apparatus.

FIG. 10 is a block diagram of a microfluidic processing system 115. Processing system 115 may be designed to allow for control of programmable dielectrophoretic array (PDA)

116 that serves as the site for microfluidic interactions and may be constructed in accordance with the present disclosure. In view of its broad functionality, PDA 116 may serve a role, in the field of fluidic processing, analogous to the role played by a Central Processing Unit in the field of computers.

Coupled to PDA 116 are fluidic sensors 122. Fluidic sensors 122 may measure and monitor fluid products from, in, or on PDA 116. For instance, fluidic sensors 122 may measure and identify reaction products and may quantify reactions between packets. In one embodiment, fluidic sensors 122 may include an optical microscope or one or more sensors (chemical, electrochemical, electrical, optical, or the like), but any other suitable monitoring device known in the art may be substituted therewith. For example, fluidic sensors 122 may be an electrochemical sensor that monitors the presence and concentration of electroactive (redox-active) molecules in a packet solution. An electrochemical sensor may take the form of two or more microelectrodes. In a three-electrode configuration, for example, electrodes may correspond to working, reference, and counter electrodes. A packet to be analyzed may be moved to be in contact with the three electrodes. A voltage signal may be applied between the working and reference electrode, and the current between the working and counter electrode may be monitored. The voltage-current relationship allows for the determination of the presence or absence, and concentration of electro-active molecules in the packet solution. Also attached to PDA 116 may be suitable material injection and extraction devices 120 coupled to appropriate inlet or outlet ports of PDA 116 (not shown in FIG. 10). Such devices may be any suitable structure allowing ingress to and egress from PDA 116.

In electrical communication with PDA 116 may be PDA voltage drivers 126 and dielectric position sensors 124. PDA voltage drivers 126 may be adapted to drive electrodes within PDA 116 so that an electric field may be established that sets up manipulation forces that manipulate one or more packets of material within PDA 116 to promote microfluidic interactions. In one embodiment, PDA voltage drivers 126 may include a signal generator and switching network as described in relation to FIG. 7. Dielectric position sensors 124 may measure positions of packets within PDA 116. In one embodiment, dielectric position sensors 124 may include measuring devices connected to appropriate sensors that may determine a position of one or more packets of material by sensing, for instance, a change in impedance between neighboring impedance sensing electrodes within PDA 116 and by correlating that change in impedance with a packet positioned adjacent the neighboring sensors according to the teachings of the present disclosure.

Coupled to packet injection and extraction devices 120, PDA voltage drivers 126, and dielectric position sensors 124 may be computer interface 128. Computer interface 128 may be configured to allow host computer 130 to interact with PDA 116. In one embodiment, computer interface 128 may be a digital or analog card or board that may analyze impedance data to obtain a packet distribution map.

In the embodiment of FIG. 10, host computer 130 may be coupled to computer interface 128 to provide for control of PDA 116. Host computer 130 may be coupled to position tracking agent 132 and to low-level control agent 134. Position tracking agent 132 may be adapted to store, process, and track positions of packets within the fluidic processor PDA 116. Low-level control agent 134 may be configured to provide instructions to host computer 130 from library interface 136 and software interface 138. Library interface 136 may hold various sets of subroutines for programmably manipulating packets of materials on PDA 116. Software interface 138 that may allow for custom programming of instructions to be executed by the fluidic processor PDA 116 to programmably manipulate packets. Alternatively established programs of manipulation instructions for specific fluid processing tests may be read from stored data and executed by the PDA fluid processor 116.

Figure 11:
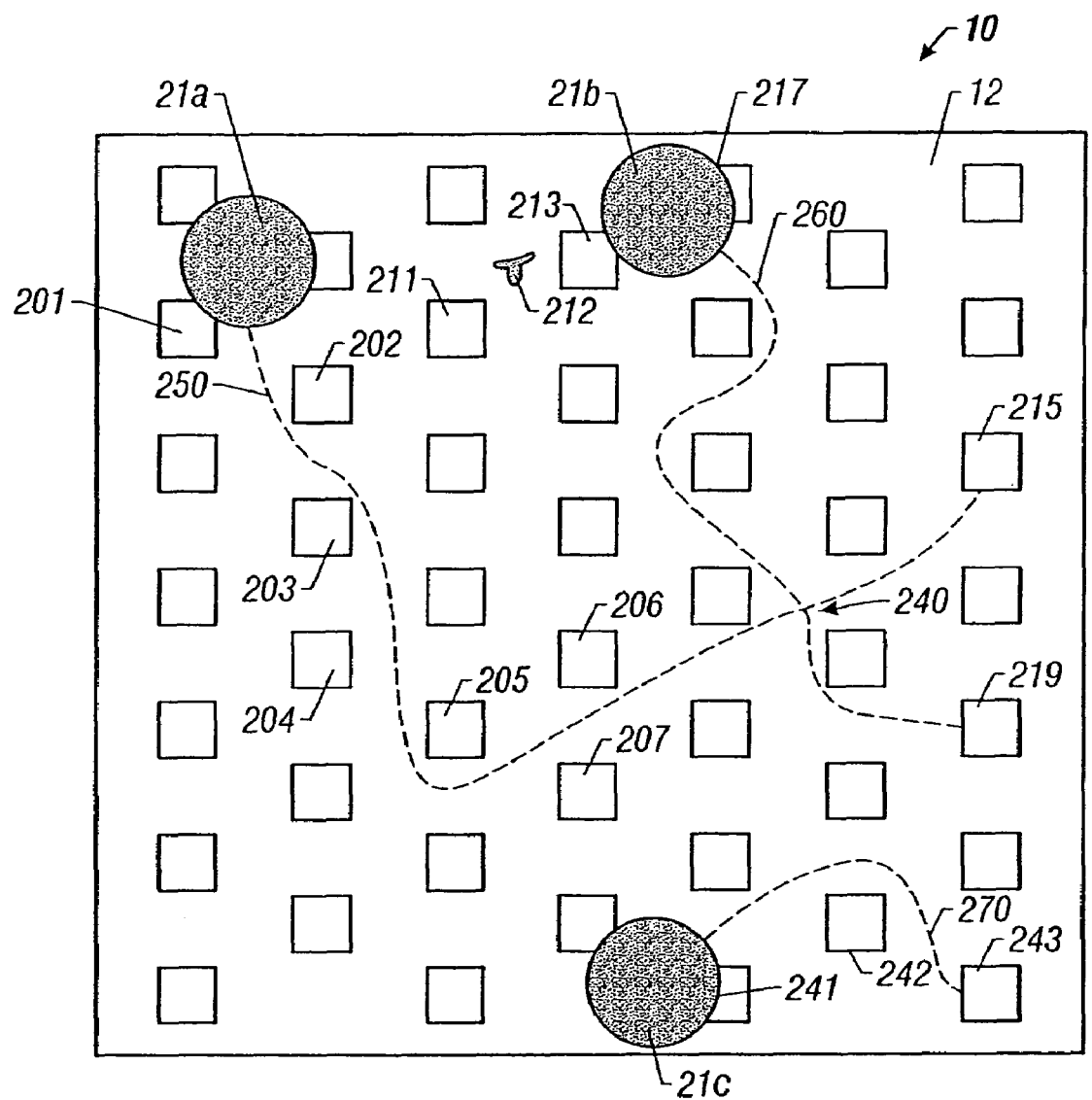
FIG. 11 is a top view of a microfluidic device showing a microfluidic process according to one embodiment of the presently disclosed method and apparatus.

FIG. 11 illustrates operation of the presently disclosed method and apparatus. In FIG. 11, open squares represent electrodes of an integral array. However, it is contemplated that the description below applies equally well to a device utilizing separate impedance sensing electrodes and driving electrodes.

In the illustrated embodiment, a packet 21a may be introduced onto reaction surface 12 adjacent the location represented by integral impedance sensor/electrode 201. The packet may be compartmentalized in an immiscible partitioning medium (not shown). The introduction of the packet may be accomplished using an appropriate inlet port positioned adjacent to electrode 201. Alternatively, a packet may be introduced adjacent electrode 201 by applying an appropriate signal to electrode 201 to generate an extraction force that may extract the packet from an inlet port or from an injector directly onto reaction surface 12 and adjacent to electrode 201.

Once positioned upon reaction surface 12, packet 21a may be made to move along a predetermined path indicated by dashed line 250. A path may be specified in a number of different ways. In one embodiment, a user may specifically define a path. For instance, one may specify a path, through appropriate programming of a controller or processing system, such as the one depicted numeral 250. Alternatively, a user may specify a starting position and an ending position to define a path. For instance, a user may specify that packet 21a is to be introduced adjacent electrode 201 and end at a location adjacent electrode 215. Alternatively, one may specify a starting and ending is location with specific path information in between. For instance, a user may specify a starting position, an ending position, and a wavy path in between. As can be seen from FIG. 11, the path may have any arbitrary shape and it may be programmed in any number of ways.

To move packet 21a generally along the path, electrical signals may be suitably switched to integral impedance sensors/electrode pairs so that programmable manipulation forces may be created that act upon packet 21a to propel it generally along the specified path. As discussed earlier, the signals may be varied in numerous ways to achieve the proper manipulation force. In the illustrated embodiment, applying voltage signals to electrode pairs 202 and 203 may create an attractive dielectrophoretic force that moves packet 21a from electrode 201 towards electrode 203 generally along path 250. As packet 21a moves generally along a specified path, the integral array may measure impedances to map the position of the packet upon reaction surface 12. Knowing the position of a packet allows manipulation forces to be directed at appropriate positions to achieve a desired microfluidic processing task or interaction. In particular, knowing a position of a packet allows an appropriate signal to be switched to an appropriate electrode or electrode pair to generate a manipulation force that further propels or interacts the packet according to one or more instructions.

As packet 21a moves from electrode 201 towards electrode 203, the impedance between electrode 202 and electrode 203 may change value, indicating that packet 21a is between, or partially between, those two electrodes. The impedance may be measured as described in FIG. 3. A controller or processing system (not shown in FIG. 11) may register the location of packet 21a and may apply a signal, for instance, to electrode pairs 204 and 205, creating an attractive dielectrophoretic force which propels packet 21a towards those electrodes generally along path 250. As the impedance between electrode 204 and electrode 205 changes value, a controller or processing system may apply a signal to electrodes 206 and 207 to propel packet 21a along path 250. As packet 21a continues along path 250, the impedance between electrode 206 and electrode 207 may change value, indicating the presence of packet 21a adjacent that location along the array. Thus, as packet 21a moves along path 250, a controller or processing system may constantly monitor the position of the packet by measuring impedance between electrode pairs and adjust electrical signals to an appropriate electrode or electrode pair (and hence, adjust manipulation forces) to continue to propel the packet further along the specified path.

Measuring an impedance between pairs of electrodes not only allows a position of a packet to be determined, but it also allows for the determination of a location of an obstruction or blockage upon reaction surface 12. For example, measuring the impedance between electrodes 211 and 213 may indicate the presence of obstruction 212. By noting the position of obstruction 212, a controller or processing system may re-route one or more packets around the obstruction so that no interference with microfluidic processing interactions occurs. For example, if a path is specified that passes through an area occupied by obstruction 212, a controller or processing system may modify electrical signals to propel a packet generally along the specified path while avoiding the obstruction. For instance, a stronger or weaker signal may be sent to one or more electrodes or electrode pairs near obstruction 212 to steer a packet clear of the blockage while still maintaining, generally, the path that was originally specified, and more particularly, the originally specified end point A controller or processing system according to the presently disclosed method and apparatus may be programmed to scan for several obstructions and/or packets. Such a scan may build up a distribution map, showing the location(s) of various packets and/or obstructions on an entire reaction surface 12 or a portion thereof. Such a distribution map may be a virtual map, stored, for example, in a computer memory or display. Turning again to FIG. 11, impedances of all electrode pairs adjacent to path 250 may be measured to determine if an obstruction blocks that path or if a packet lies somewhere in that area. If the path is determined to be clear (e.g., if all the electrode pairs show an impedance value indicating a clear area), a packet may be safely propelled generally along the path while avoiding any interactions with other packets and/or obstructions. However, if an obstruction is discovered, several different actions may be taken. In one embodiment, the is user may be notified that a blockage exists along the specified path. The user may then specify a different path or give another appropriate instruction. In another embodiment, the controller or processing system may determine if the obstruction may be avoided while still maintaining generally the same specified path. If possible, electrical signals may be modified and delivered to an electrode or electrode pairs to generate appropriate electrical field distributions that set up proper manipulation forces that will aid in avoiding the obstruction. Because, at least in part, of this ability to constantly measure positions and responses of packets during manipulation, a controller or processing system may be capable of monitoring the integrity of fluidic processing, reporting and correcting any errors that may occur.

FIG. 11 also depicts how processing may be carried out on two packets. In the illustrated embodiment, a second packet 21b begins on reaction surface 12 near electrode 217. A second path, path 260, may be specified that ends at electrode 219. As can be seen, paths 250 and 260 may cross at interaction point 240. At interaction point 240, the two packets may interact in many ways as illustrated, for example, in FIG. 12. The interaction may include, but is not limited to, fusing, merging, mixing, reacting, dividing, splitting, or any combination thereof. For instance, the two packets may interact at interaction point 240 to form one or more intermediate or final reaction products. Those products may be manipulated in the same or in a similar manner as the two original packets were manipulated.

FIG. 11 also depicts how maintenance may be performed upon reaction surface 12. A maintenance packet 21c adapted to perform maintenance upon reaction surface 12 may be introduced onto reaction surface 12 by a maintenance port (not shown in FIG. 11). A maintenance port may be similar to an inlet port in structure but may be dedicated to the introduction of one or more maintenance packets 21c designed specifically, for instance, to clean or maintain reaction surface 12, a surface coating, or one or more electrodes or sensors. Maintenance packet 21c may also react with an obstruction in such a way as to remove that obstruction. As illustrated, maintenance packet 21c may begin near electrode 241. It may then be propelled along path 270, providing maintenance, perhaps, to electrodes 242 and 243. Maintenance packet 21c may be propelled back to a maintenance port, extracted from reaction surface 12, and later used again, or it may discarded at an outlet part.

Figure 12:
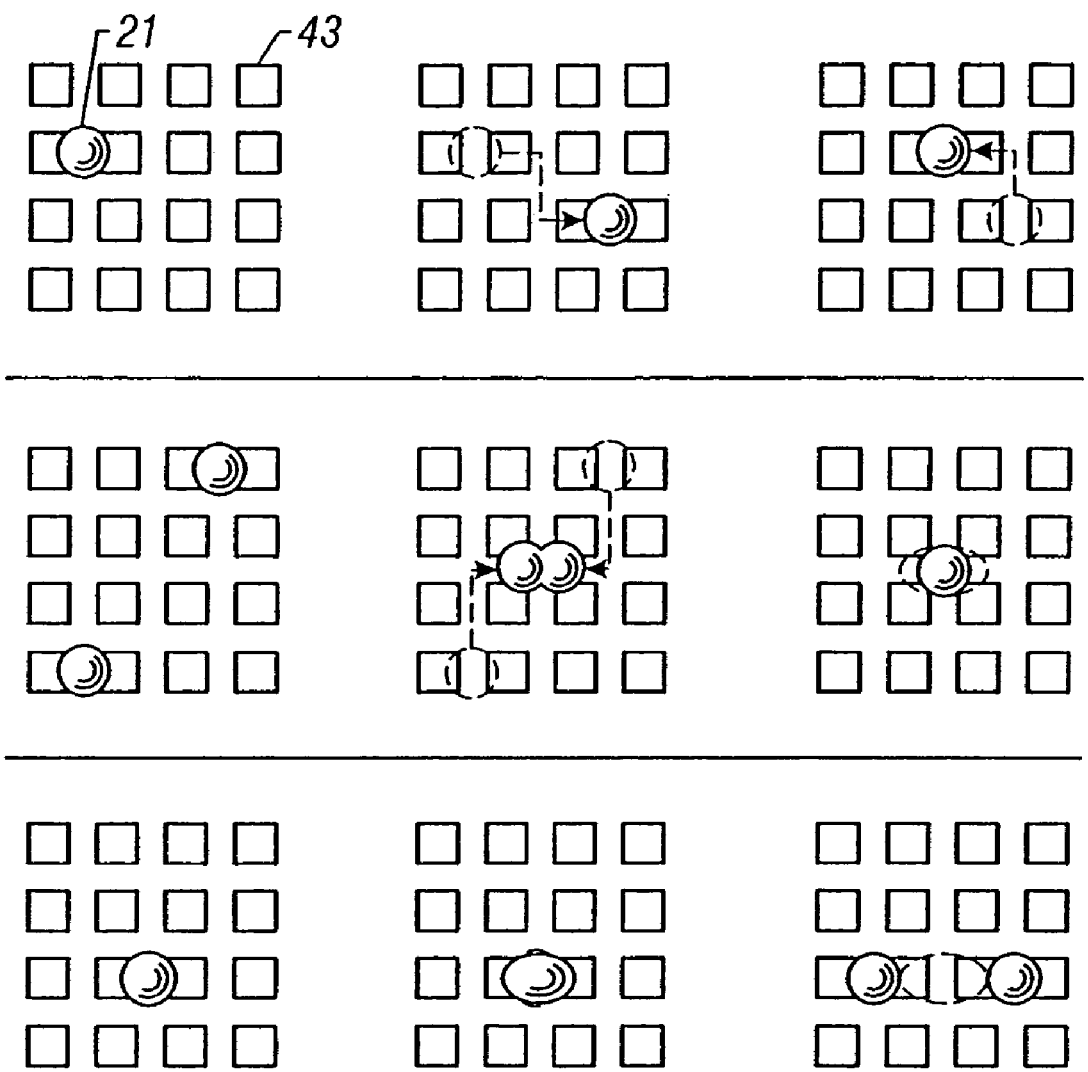
FIG. 12 illustrates certain packet interactions according to one embodiment of the presently disclosed method and apparatus.

FIG. 12 demonstrates several different possible fluidic interactions that may be carried out using the presently disclosed method and apparatus. In the illustrated embodiment, packets 21 (only one is labeled for convenience) reside upon a reaction surface 12 having an integral array 43 (only one electrode is labeled for convenience). In the top pane of FIG. 12, there is shown an interaction in which a single packet is manipulated on the reaction surface by moving the packet in a programmed fashion. In the middle pane, two packets, starting at different locations upon the reaction surface, are directed, via appropriate electrical signals, to come together at a specified location (near the center of the array) to fuse together, for example, to initiate a reaction. The fused packet may be manipulated just as the original packets were manipulated. For instance, the fused packet may be moved to various locations or it may fuse again with another packet(s). Shown in the bottom pane of FIG. 12 is a splitting interaction. As shown, a single packet is subjected to different programmable manipulation forces that cause the packet to split into two distinct packets. Such an interaction may be accomplished by, first, noting the position of the packet to be split, and then by applying appropriate signals to electrode pairs to generate two or more opposing forces that cause the packet to split apart.

Figure 13:
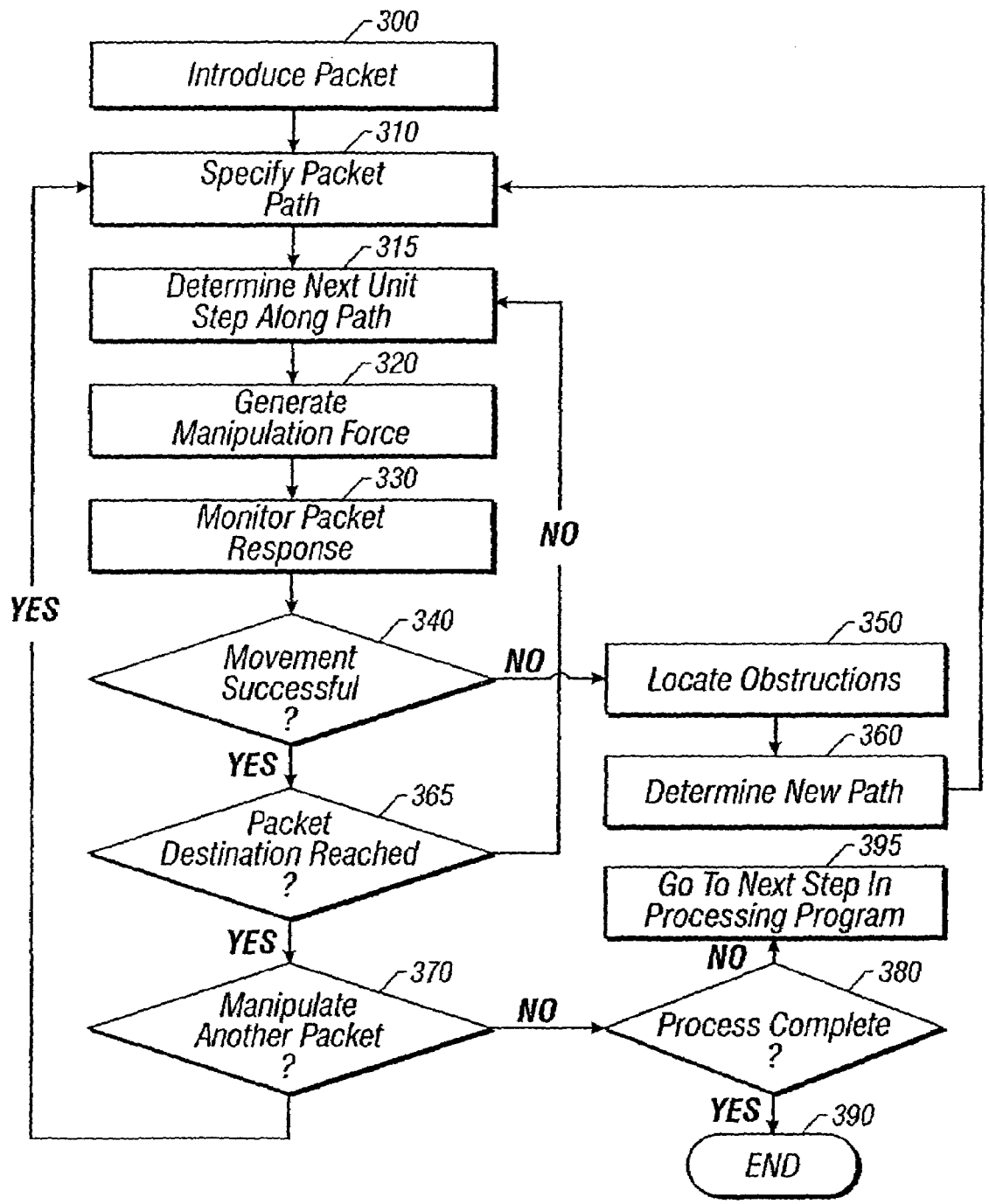
FIG. 13 is a flow chart showing a microfluidic process according to one embodiment of the presently disclosed method and apparatus.

FIG. 13 is a flowchart showing one embodiment of a method of operation. A material may be introduced onto a reaction surface and compartmentalized to form one or more packets in step 300. Multiple materials may be introduced at different locations along reaction surface 12 to form a plurality of packets. A path may be specified as in step 310. The path may be designed to accomplish any type of microfluidic processing, manipulation, or interaction. Different reactions may be performed in serial or in parallel according to different paths. Instructions governing such processing may be embodied in the pseudo-code that may be routed through computer interface 128 of FIG. 10. Illustrative code may read as follows:

Example: AvidinActin.PSL
Use inlet(1-3), outlet(1-2)
Inlet(1) is actin
Inlet(2) is avidin
Inlet(3) is enzyme
Outlet(1) is polymer
Outlet(2) is waste
Matrix(1, 2) is accumulator
Clean
Do
   Sactin=(Pull actin)//pull a new packet on the next
   Savidin=(Pull avidin)//available matrix element next to
   Senzyme=(Pull enzyme)//the inlets
   Move Sactin into accumulator//merges components and enzyme
   Move Savidin into accumulator//in a single packet
   Move Senzyme into accumulator
   Wait 1000 ms
   ShiftRow accumulator.row,+1//drag packet left into polymer outlet
   Move 0.5*accumulator into (2, accumulator.column)//drag half packet to row 2
   ShiftRow 2,+1//drag packet left into waste
Loop Until polymer.count=10//number of packet at polymer outlet=10
Clean In step 315, computer 80 of FIG. 6 or any other suitable device may determine the next unit step along the path specified in step 315. In other words, a path may be broken down into unit steps and the next unit step or steps may be determined with respect to the specified path. In step 320, a programmable manipulation force is generated on reaction surface 12 through the use of any of the mechanisms disclosed herein. The programmable manipulation force may manipulate the one or more packets according to instructions from a user. In step 330, the response(s) of the one or more packets may be monitored. This step may include measuring an impedance on the reaction surface as discussed herein. In particular, one may determine whether the one or more packets moved to where they were supposed to, or whether they interacted as instructed. In step 340, it may be determined if the packet movement was successful—that is, it may be determined whether the packet ended up at a location corresponding to the unit step determined in step 315.

If a packet movement was successful (i.e., if the packet responded correctly to the programmable manipulation force(s)), then it may be determined, by comparison with the specified path, whether or not the packet destination has been reached. In other words, it may be determined if the packet has moved to the end location of the specified path. If the destination has not been reached, the next unit step movement may be determined at step 315 and steps 320, 330, 340, and 365 may be repeated. If the destination has been reached, it may be determined whether another packet is to be manipulated in step 370. This step may include a user prompt. If no further packets are to be manipulated, it may be determined whether fluidic processing is complete in step 380. If yes, the process may be ended at step 390. Step 390 may include the collecting of one or more packets, further analysis, throwing away of the reaction surface, or any procedure described herein. If the processing is not complete, the next step of processing may be determined in step 395. The next step may entail, for example, the introduction of another packet, the specification of another path, or any other step of FIG. 13.

If a packet manipulation is unsuccessful (i.e., if the applied programmable manipulation force(s) did not produce a desired interaction or movement along a specified path as indicated by step 340), one may locate an obstruction upon the reaction surface as indicated in step 350 and as taught herein. After locating any obstructions, a new, modified path may be determined or specified as indicated by step 360, leading to step 310.

As mentioned with relation to FIG. 1, the present disclosure contemplates that many different types of forces may be utilized as a manipulation force for promoting fluidic interactions among packets of material on a reaction surface. Specifically, suitable forces other than dielectrophoresis include electrophoretic forces, optical forces, mechanical forces, or any combination thereof. Below are discussed embodiments of the present disclosure dealing with electrophoretic and optical manipulation forces.

Programmable Electrophoretic Array (PEA)

A fluidic processing system incorporating a programmable electrophoretic array may be constructed according to the present disclosure. As used herein, "programmable electrophoretic array" (PEA) refers to an electrode array whose individual elements can be addressed with DC, pulsed, or low frequency AC electrical signals (typically, less than about 10 kHz) electrical signals. The addressing of electrode elements with electrical signals initiates different field distributions and generates electrophoretic manipulation forces that trap, repel, transport or perform other manipulations upon charged packets on and above the electrode plane. By programmably addressing electrode elements within the array with electrical signals, electric field distributions and electrophoretic manipulation forces acting upon charged packets may be programmable so that packets may be manipulated along arbitrarily chosen or predetermined paths. A PEA may utilize electrophoretic forces in DC or low-frequency (typically, less than about 10 kHz) AC electrical fields. Such electrophoretic forces may be used instead of, or in addition to, another manipulation forces such as dielectrophoresis.

Negative or positive charges may be induced or injected into fluid packets. The charged packets may be moved or manipulated by electrophoretic forces generated by an electrode array fabricated on an inner surfaces of a chamber in accordance with this disclosure. The electrode array, termed a programmable electrophoretic array (PEA), may consist of uniformly or non-uniformly spaced electrode elements. Individual electrode elements may be independently addressable with DC, pulsed, or low frequency AC electrical signals (<about 10 kHz). Characteristic dimensions of individual electrode elements may be of any size but, in one embodiment, may lie between 0.2 micron and 10 mm. Individual electrode elements may take similar or different geometrical forms such as squares, circles, diamonds, or other shapes. Programmably switchable electrical signals may be applied to individual electrode elements so that a programmable electrical field distribution may be generated. Such a distribution may impose electrophoretic forces to trap, repel, transport or manipulate charged packets in a partitioning medium. Further, electrical signals may be applied to such an array so that a packet may be broken down to two or more packets. The programmability of a PEA may be reflected in the fact that the electric field distributions and electrophoretic forces acting on charged packets may be programmable so that charged packets may be trapped or repelled or transported along arbitrarily chosen paths in the partitioning medium, and that a PEA may be programmed to perform different reactions in series or in parallel where different manipulation protocols of packets (differing in size, number, and/or reagent type concentration) may be required. As with PDA surface modification, if a dielectric layer coating is applied to the surface of a PEA to modify interaction forces between packets reaction surfaces, the dielectric layer may be made sufficiently thin (typically 2 nm to 1 micron) to allow for electric field penetration.

Optical Manipulation

Optical tweezers (which may consist of a focused laser beam with a light intensity gradient) may be also be used for trapping and manipulating packets of material. Optical manipulation requires that the refractive indices of the packets be different from that of their suspending medium, for instance, a partitioning medium as described herein. As light passes through one or more packets, it may induce fluctuating dipoles. Those dipoles may interact with electromagnetic field gradients, resulting in optical forces directed towards or away from the brighter region of the light. If their refractive indices are higher than that of the partitioning medium, packets may be trapped in a bright region, and when the laser light moves with respect to the partitioning medium, packets may follow the light beam, allowing for optical manipulation forces. Conversely, if the packets have refractive indices smaller than their partitioning medium, they will experience forces directing them away from bright regions.

Therefore, if packets have different refractive indexes from that of the partitioning medium (e.g., water packets in air or oil), optical tweezers may exert forces on them. Therefore, to manipulate and interact packets, a microscope or other optical system incorporating one or more laser tweezers may be used. A chamber containing a partitioning medium in accordance with the present disclosure may be placed into such an optical system. Following the introduction of packets of material into the chamber, laser tweezers may be used to trap packets. By moving the focal point of the optical tweezers with respect to the partitioning medium (e.g., moving a stage holding the thin chamber containing the partitioning medium whilst fixing the position of laser tweezers and/or by focusing the laser beam to different depths in the partitioning medium), packets may be manipulated as described herein. Through the use of apparatus such as a computer-controllable, multi-axis translation stage, the movement of the optical tweezers with respect to the suspending medium may be programmed or automatically controlled. Thus the optical tweezer may be moved, with respect to the medium, along any arbitrarily chosen or predetermined paths. By doing so, packets under the influences of the optical tweezers may be manipulated along any arbitrarily chosen or predetermined paths.

EXAMPLE 1

Aqueous materials have been compartmentalized to form packets using hydrophobic liquids as a partitioning medium. Partitioning mediums so used have included decane, bromodocane, mineral oil, and 3 in 1™ oil. Packets have been formed by briefly sonicating about 3 milliliters of the hydrophobic liquid to which had been added 20 to 50 microliters of aqueous medium. Aqueous media tested have included deionized water, tap water (electrical conductivity of about 40 mS/m) and phosphate buffered saline (PBS) solution.

EXAMPLE 2

Aqueous packets suspended in mineral oil, bromodoecane and 3 in 1™ oil have been collected by dielectrophoresis by applying sinusoidal signals to gold-on-glass electrode arrays having 20, 80 and 160 micron spacing, respectively. The 20-micron electrode array consisted of parallel line electrodes (20 microns in width and spacing). The 80 and 160 micron electrode arrays were of the interdigitated, castellated geometries. Aqueous packets were collected at electrode edges or tips when AC voltage signals between 100 Hz and 20 MHz were applied. Applied voltages were from 10 to 100 V peak-to-peak. The formation of pearl-chains of water packets has also been observed.

EXAMPLE 3

Aqueous packets in hydrophobic suspension have been brought together and fused under the influence of dielectrophoretic forces on the same electrode arrays used in Example 2.

EXAMPLE 4

Packets have been moved from one electrode element to another under influence of dielectrophoretic forces when the AC electrical field is switched on an addressable array of parallel line electrodes having 20 micron width and spacing.

EXAMPLE 5

Sensitive AC impedance monitors have been built for use with microelectrode arrays. Such monitors may provide for sensitive dielectric sensing of packet positions.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims. Moreover, the different aspects of the disclosed apparatus and methods may be utilized in various combinations and/or independently. Thus the invention is not limited to only those combinations shown herein, but rather may include other combinations.

What is claimed is:

1. A method for manipulating a packet, comprising:
positioning a packet on a reaction surface that is coupled to a force generator, the reaction surface and force generator configured to generate dielectrophoretic forces capable of moving a packet about the reaction surface along arbitrarily chosen paths;
reading machine-executable manipulation instructions for a specific fluid processing test from stored data;
executing the manipulation instructions to generate a dielectrophoretic force that moves the packet upon the reaction surface according to the fluid processing test; and
sensing with a position sensor a position of the packet, the position sensor configured to track the position of a packet along arbitrarily chosen paths about the reaction surface.

2. The method of claim 1, further comprising determining if the position of the packet is in error relative to the specific fluid processing test.

3. The method of claim 2, where determining if the position of the packet is in error comprises determining whether movement of the packet corresponds to a path specified by the manipulation instructions.

4. The method of claim 3, where the path specified by the manipulation instructions comprises an initial position and a final position.

5. The method of claim 2, further comprising reporting the error if an error is determined.

6. The method of claim 1, where the packet comprises a fluid packet, an encapsulated packet, or a solid packet.

7. The method of claim 1, where generating a dielectrophoretic force comprises applying a driving signal to one or more driving electrodes arranged in an array.

8. The method of claim 1, where sensing comprises applying a sensing signal to one or more impedance sensing electrodes arranged in an array.

9. The method of claim 1, further comprising interacting the packet with another packet, where interacting comprises moving, fusing, merging, mixing, reacting, metering, dividing, splitting, sensing, collecting, or any combination thereof.

10. The method of claim 1, where the manipulation instructions are part of a subroutine within a library interface.

11. The method of claim 1, where the manipulation instructions are custom instructions generated using a software interface.

12. A system for manipulating a packet, comprising:
a programmable dielectrophoretic array (PDA);
a computer;
a library interface coupled to the computer and configured to store subroutines for programmably manipulating packets within the PDA;
a software interface coupled to the computer and configured to allow custom programming of instructions for programmably manipulating packets within the PDA;
a position tracking agent coupled to the computer and configured to store, process, and track positions of packets within the PDA; and
a low-level control agent coupled to the computer and configured to provide instructions to the computer;
where the system is configured to generate dielectrophoretic forces capable of moving the packet about the reaction surface along arbitrarily chosen paths; and
where the position tracking agent is configured to track the position of a packet along arbitrarily chosen paths about the reaction surface.

13. An apparatus for manipulating a packet, comprising:
a fluidic device comprising a reaction surface, driving electrodes that generate a dielectrophoretic force on a packet upon the reaction surface, and sensing electrodes that detect a position of the packet upon the reaction surface; and
an integrated circuit coupled to the fluidic device and configured to control the driving and sensing electrodes, the fluidic device configured to generate dielectrophoretic forces capable of moving a packet about the reaction surface along arbitrarily chosen paths, and the fluidic device configured to track the position of a packet along arbitrarily chosen paths about the reaction surface.

14. The apparatus of claim 13, further comprising an interface board coupled to the fluidic device and integrated circuit.

15. The apparatus of claim 13, the integrated circuit being configured to adjust driving signals to the driving electrodes according to positions of packets determined by the sensing electrodes.

16. The apparatus of claim 15, the integrated circuit being configured to adjust the driving signals to move the packets along arbitrarily chosen paths.

* * * * *

UNITED STATES PATENT AND TRADEMARK OFFICE
CERTIFICATE OF CORRECTION

| | |
|---|---|
| PATENT NO. | : 7,641,779 B2 |
| APPLICATION NO. | : 11/135615 |
| DATED | : January 5, 2010 |
| INVENTOR(S) | : Becker et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this

Sixteenth Day of November, 2010

David J. Kappos
*Director of the United States Patent and Trademark Office*